United States Patent
Song

(10) Patent No.: US 11,668,266 B2
(45) Date of Patent: Jun. 6, 2023

(54) TOTAL RECYCLING SYSTEM OF CAPTURING, CONVERSION AND UTILIZATION OF FLUE GAS FROM FACTORY, POWER PLANT AND REFINERY

(71) Applicant: Weining Song, Suzhou (CN)

(72) Inventor: Weining Song, Suzhou (CN)

(*) Notice: Subject to any disclaimer, the term of this patent is extended or adjusted under 35 U.S.C. 154(b) by 395 days.

(21) Appl. No.: 16/887,044

(22) Filed: May 29, 2020

(65) Prior Publication Data
US 2020/0291901 A1 Sep. 17, 2020

Related U.S. Application Data

(63) Continuation of application No. PCT/CN2018/114521, filed on Nov. 8, 2018.

(30) Foreign Application Priority Data

Nov. 29, 2017 (CN) .......................... 201711229415.6

(51) Int. Cl.
| | |
|---|---|
| *F02M 21/02* | (2006.01) |
| *F23C 9/00* | (2006.01) |
| *C08J 9/12* | (2006.01) |
| *B01D 53/14* | (2006.01) |

(52) U.S. Cl.
CPC ..... *F02M 21/0215* (2013.01); *B01D 53/1418* (2013.01); *B01D 53/1475* (2013.01); *C08J 9/122* (2013.01); *F02M 21/0218* (2013.01); *F23C 9/00* (2013.01); *B01D 2258/0283* (2013.01); *C08J 2203/06* (2013.01); *Y02T 10/12* (2013.01)

(58) Field of Classification Search
CPC ............ B01D 53/1418; B01D 53/1475; B01D 2258/0283; C08J 9/122; C08J 2203/06; F23C 9/00
USPC .......................................................... 518/702
See application file for complete search history.

(56) References Cited

FOREIGN PATENT DOCUMENTS

CN 102618001 A * 8/2012

OTHER PUBLICATIONS

CN-102618001-A English Translation (Year: 2012).*

* cited by examiner

*Primary Examiner* — Anita Nassiri-Motlagh

(57) ABSTRACT

A total recycling system of capture, conversion and utilization of flue gas from factory, power plant and refinery. A combined decontamination and dust removal unit removes dust and oxides; a capture subsystem captures $CO_2$; a water unit recovers water; a hydrogen unit decomposes water into hydrogen and oxygen, and the oxygen is fed into a water gas unit to support combustion and extract hydrogen; a conversion subsystem enables a catalytic reaction between $CO_2$ and hydrogen to convert into methanol and diol; an utilization subsystem makes a supercritical $CO_2$ nanocellulose slurry, then to be blended with other material particles and extruded to form a supercritical $CO_2$ nanocellulose foam; an energy subsystem is configured with solar energy, wind energy, and supplements energy by means of residual heat and hydrogen power generation; the system achieve carbon dioxide emission's reduction, conversion and utilization, thoroughly improve air pollution and green house effects.

7 Claims, 10 Drawing Sheets

TOTAL RECYCLING SYSTEM OF CAPTURING, CONVERSION AND UTILIZATION OF FLUE GAS FROM FACTORY, POWER PLANT AND REFINERY

CROSS-REFERENCE TO PRIOR APPLICATION

The present application is a continuation-application of International (PCT) Patent Application No. PCT/CN2018/114521 filed on Nov. 8, 2018, which claims foreign priorities of Chinese Patent Application No. CN201711229415.6, filed on Nov. 29, 2017, the entire contents of which are hereby incorporated by reference.

TECHNICAL FIELD

The technical field relates to capturing, conversion and utilization of flue gas, and more particularly relates to a total recycling system of capturing, conversion and utilization of flue gas from factory, power plant and refinery.

DESCRIPTION OF RELATED ART

Since the middle of the 20th century, more than half of global warming has been caused by human activities, and the credibility of this conclusion is above 95%. Global warming is undoubted over the past 100 years. From 1880 to 2012, the average global surface temperature increased by 0.85 degrees Celsius; in the northern hemisphere, 1983-2012 may be the warmest 30-year of the last 1400 years. In the past 60 years, the average surface temperature in China has increased by 1.38 degrees Celsius, and the average temperature has increased by 0.23 degrees Celsius every decade, which is almost twice the global average. in recent years, global high-temperature events have increased significantly. Droughts and flooding rains have occurred frequently. Most of the landfall typhoons hit China. Nearly half of the landfall typhoons have reached the 12th level and the number of the landfall typhoon which has nearly doubled in the 1990s has increased.

Climate change have profound impacts on natural ecosystems and human society to affect everyone; changes in global precipitation and snow and ice caused by climate change are exacerbating the lack of freshwater resources; climate change causes ocean acidification and exacerbates existing human health problems, leading to increase human mortality in some areas; global warming has affected natural ecosystems and economic and social development possessing serious threats to traditional and non-traditional security such as global food security, water security, ecological security, environmental safety, energy security, major engineering safety.

The extent of global warming in the future depends mainly on the cumulative carbon dioxide emissions. Even if humans stopped emitting greenhouse gases, climate change and related impacts caused by greenhouse gases emissions in the past will continue for many centuries. Near-term and long-term mitigation measures will effectively limit the impact from climate change later in the century. At the end of the century, the average global surface temperature may be 4 degrees Celsius above pre-industrial levels without further measures. If the global greenhouse gases concentration is controlled within 450 ppm $CO_2$ equivalent, the temperature rise at the end of the century may be controlled within 2 degrees Celsius. To this end, by 2050, anthropogenic greenhouse gas emissions should be reduced by 40% to 70% compared to 2010, and zero emissions should be achieved by 2100.

By 2015, China has surpassed the United States to become the world's largest carbon dioxide emitter. The global carbon dioxide emissions reached about 36 billion tons, wherein carbon dioxide emissions in China was 10.6 billion tons, and reached 110 billion tons in 2016.

The problems existed in the prior art are:

A. The recovery of carbon dioxide from flue gas and treatment of the flue gas are usually for a single component or a part of components, and the degree of resource utilization is low; exhaust gas, waste liquid and solid waste are still generated, and the impact on climate, environment and economy remains the same;

B. In the sector of carbon dioxide emission, as shown in Table 1, the energy and industry emissions account for more than 52% of the global carbon dioxide emission; while the carbon

| Table of carbon dioxide emissions by global industries (%) | | | | | | | |
|---|---|---|---|---|---|---|---|
| Industry | Energy | Industry | Transport | Agriculture | Forestry | Building | Rubbish | Other |
| $CO_2$ emissions | 35 | 17 | 13 | 11 | 10 | 7 | 4 | 3 | dioxide content in the air ranges from 300 PPM to 408 PPM (0.03% to 0.0408%), therefore, the effect of collecting carbon dioxide from air on the control of the entire carbon dioxide emissions is negligible, resulting in huge investment in the prior art, and biases of the direction of investment and research and development could appear;

C. Carbon trading and carbon dioxide utilization cannot achieve the absolute reduction on carbon dioxide, most carbon dioxide utilization is the cyclic carbon dioxide utilization, because the applied carbon dioxide will eventually return to the atmosphere again in gaseous phase, such as: soda, dry ice, fire extinguisher, alkali, sugar industry, etc., it does not achieve the goal of actually recycling carbon dioxide;

D. According to the molecular structure characteristics of carbon dioxide, it is difficult to decompose or convert carbon dioxide into methanol, glycol chemical products and the process conditions is complicated, the energy consumption is high, and because of the high cost, modular utilizations cannot actually achieved;

E. The economic value of market for carbon dioxide utilization products is low and there is no sufficient profit to pay the cost of continuous manufacturing the products of the utilization project and the utilization enterprise;

F. Not only a large amount of carbon dioxide but also dust are emitted by Heating system and coat-fired power plants to increase PM2.5 and severe smog composed of airborne dust, sulfuric acid, nitric acid, organic hydrocarbons and other particles. The sulphur dioxide, nitrogen oxides and atmospheric particulate matter (PM2.5) are the three main components of smog, the first two components are gaseous pollutants, the first two components addition on particulate matter is the main culprit for aggravating smog pollution;

G. Because the unstable power of solar energy and wind energy and high cost of voltage regulators, it is difficult to connect solar energy and wind energy, and cannot realize its economic value. According to statistics, China has wind and solar energy waste which were worth 60 billion RMB because it cannot be used in the network every year; hydrogen production from wind power does not have practical utilization value due to high transportation price and high risk.

SUMMARY OF THE INVENTION

In order to solve the above technical problems, the present invention provides a total recycling system of capturing, conversion and utilization of flue gas from factory, power plant and refinery. According to the defects in the prior art, the system is designed as a combination technology of a total recycling of flue gas from factory, power plant and refinery and conversion into high added value product. The system treats the flue gas emitted from thermal power plants, thermal power plants, oil processing plants, steel plants, cement (phosphorus magnesium) plants, chemical plants, etc. emitting $CO_2$. in particular, converting $CO_2$ from thermal power plants in the energy industry and petroleum processing plants in the industrial sector, the two main industry, to high value-added product for resource utilization to achieve absolute reduction and conversion of carbon dioxide; and to develop innovative, low-cost, high-efficiency carbon dioxide conversion process for increasing conversion rate. And this system converts carbon dioxide to high value-added products with solar energy and wind power generation system to cut off the source of smog and PM2.5 to be a closed carbon loop; the regenerative energy complements the fossil energy to thoroughly solve the problem of air pollution and global greenhouse effect.

In order to achieve the above object, the technical scheme of the present invention is as follows: a total recycling system of capturing, conversion and utilization of flue gas from factory, power plant and refinery, referred to as a flue gas total recycling system, comprising an energy subsystem, a capture subsystem, and a conversion subsystem, an utilization subsystem, a water gas unit, a carbon dioxide capture unit, a hydrogen production unit, a water recovery unit, a combined decontamination and dust removal unit, a supercritical refining and preparation of nanocellulose unit, a supercritical carbon dioxide nanocellulose foaming material unit, wherein the flue gas includes dust particles, a gaseous compound, a trace element, carbon dioxide, and water vapor, wherein the gaseous compound includes at least nitrogen oxides and sulfur oxides; wherein the flue gas total recycling system removes the dust particles and the gaseous compound by the combined decontamination and dust removal unit; capturing carbon dioxide by the carbon dioxide capture unit in the capture subsystem and pressurizing the captured carbon dioxide to supercritical carbon dioxide; recovering water vapor in the flue gas by the water recovery unit; decomposing the recovered water into hydrogen and oxygen through the hydrogen production unit, and feeding the oxygen into the water gas unit for combustion support to further obtain a high-purity hydrogen through the water gas unit; reacting the captured carbon dioxide having high stability and low energy with the high-energy ethylene oxide molecule to form ethylene carbonate (EC) by the conversion subsystem, and further subjecting the ethylene carbonate to a catalytic reaction with hydrogen to obtain methanol and a glycol; providing the supercritical carbon dioxide and nanocellulose to make the supercritical carbon dioxide nanocellulose slurry by the utilization subsystem, and after adjusting the concentration of the made supercritical carbon dioxide nanocellulose slurry, combining the adjusted supercritical carbon dioxide nanocellulose slurry with the material particles to extrude into a supercritical carbon dioxide nanocellulose foam; preparing the supercritical carbon dioxide nanocellulose slurry by the supercritical refining and preparation of nanocellulose unit; preparing the supercritical carbon dioxide nanocellulose foam by the supercritical carbon dioxide nanocellulose foaming material unit; wherein the energy subsystem is configured with a solar power generation and wind a power generation to provide clean power, and the power generated by residual heat recovery power and hydrogen gas power generation is also supplemented and deployed by the energy subsystem; wherein the energy subsystems not only has the power for each subsystem and unit of the flue gas recycling system stably distributed but also provides the required power for power distribution, lighting distribution, fire distribution, monitoring power distribution, and security distribution thereof.

A. The Combined Decontamination and Dust Removal Unit the combined decontamination and dust removal unit removes dust particles, nitrogen oxides, sulfur oxides and trace elements from the flue gas by a dry adsorption tower or an alkali absorption tank and a multi-stage dust collector, the trace elements include heavy metals such as mercury, selenium, and arsenic; wherein the dust particles are used in the supercritical carbon dioxide nanoceliulose foaming material unit of the utilization subsystem as fillers in producing foams; wherein the nitrogen oxides and sulfur oxides are collected in the form of nitrate and sulfate by a sulfur oxynitride treating system for extracting and manufacturing fertilizer;

in the prior art, the combined removal process of dust and dust particles from flue gas includes: wet method, semi-dry method and dry method; wet method mainly uses oxidant oxidation technology, semi-dry method mainly includes spray dryer, electron beam method, pulse corona method and flue gas circulating fluidized bed technology; dry method mainly includes solid phase adsorption and gas phase oxidation technology; dry method has less investment in equipment than wet and semi-dry method, and does not generate secondary pollution such as waste liquid. More broad utilization prospects.

Commonly used adsorbents for dry processes include activated carbon, activated coke, zeolite molecular sieves, etc.; the key point of the dry method is how to process desulfurization, denitrification and demercuration process and the adsorbent regeneration processes at the same time, the dry method of the combined decontamination and dust removal unit is described as follows:

using active pyromagnetic supported silver-bearing zeolite and supported SCR catalyst as adsorbents, including magnetic $Fe_3O_4$ particles, silver nanoparticles, zeolite and activated coke, $V_2O_5$—$WO_3$/$TiO_2$ oxide; wherein the most commonly used SCR catalyst is $V_2O_5$—$WO_3(MoO_3)$/$TiO_2$ series ($TiO_2$ as the main carrier and $V_2O_5$ as the main active ingredient);

wherein the flue gas includes flue gas from a thermal power plant, a thermal power plant, a petroleum processing plant, a steel plant, a cement (phosphorus magnesium) plant, a chemical plant, etc., more particularly a flue gas from a coal-fired power plant, a water gas power plant, and a gas power plant;

wherein the flue gas from the flue gas source is fed into the dry adsorption tower, and adsorbed by the activated coke magnetic silver-loaded zeolite and supported by the SCR catalyst, and a combined process of sulfur removal, mercury removal and nitride removal from the flue gas is processed, and then, by passing through the multi-stage dust collector to separate the duct particles from the flue gas to obtain the pure flue gas, and the pure flue gas is conveyed into a flue gas tank to store; wherein the solid phase mixture is collected from the dry adsorption tower and the lower part of the multi-stage dust collector, and the solid phase mixture is conveyed to a magnetic separator to separate the metal from the solid phase mixture, and a magnetic catalyst is conveyed to the regenerator for catalyst regeneration and recycling, the dust is recycled to produce byproduct, the mercury is recycled separately.

The wet process of the combined decontamination and dust removal unit is described as follows: the flue gas from the flue gas source is introduced, wherein the flue gas is treated sequentially by the following steps:

1. by a SCR denitration device, using SCR catalyst: $V_2O_5$—$WO_3$ ($MoO_3$)/$TiO_2$ to selectively catalyze reduction to remove nitrogen oxides from flue gas;

2. by a waste water heat recovery device, recovering the residual heat to adjust the temperature of the flue gas to about 95° C., below the acid dew point, which is beneficial to the adsorption of trace elements and the removal of dust;

3. by a electrostatic precipitator and a bag filter, removing 90% of the solid particles of the soot;

4. by a wet-desulfurization device equipped with a spray layer of the spray coverage rate reached above 250%, absorbing and removing the sulfur oxides and the remaining nitride;

4.1. by a mechanical mist eliminator and a wet mist eliminator, eliminating mist and removing 10% of the dust again;

conveying the pure flue gas into the capture subsystem after desulfurization; conveying the desulfurized wastewater into the desulfurization wastewater treatment device;

5. in the desulfurization wastewater treatment device, the wastewater passing through a steam separator including chlorine ions and various heavy metal components is soften and concentrated by a softening concentrator, and the softened concentrated water is transferred and sprayed into the high temperature denitration flue gas to evaporate and remove crystallization dust again, so as to achieve zero discharge operation of wet desulfurization wastewater;

6. a mercury catalyst is fed into the flue gas in the electrostatic precipitator to oxidize element mercury to mercury ions by a feeder, and then removing the mercury ions and the sulfur dioxide by the sequence wet desulfurization device.

The sulfur dioxide removal rate reached 99.5%; the dust particle removal rate was 100%.

B. The Capture Subsystem the capture subsystem is used to treat the carbon dioxide and moisture from the flue gas after dust removal, desulfurization and denitration, wherein the flue gas is from the factory, the power plant and the refinery; wherein the flue gas stored in a flue gas tank respectively passes through the water recovery unit and the carbon dioxide capture unit recovering the water gas and carbon dioxide from the flue gas; the water is stored in a water tank, and carbon dioxide is stored in a carbon dioxide tank, and carbon dioxide stored in the carbon dioxide tank is converted into supercritical carbon dioxide through a supercritical pump and then stored in a supercritical carbon dioxide tank;

the carbon dioxide recovery unit of the capture subsystem comprises an absorption/desorption unit or an ammonia spray absorption tower and a purification unit; carbon dioxide is absorbed by the carbon absorbent in a absorption tower of the absorption/desorption unit, and is desorbed by a regenerated carbon absorbent in a regeneration tower, the carbon absorbent is recycled; the desorbed carbon dioxide of the regeneration tower is sequentially subjected to residual sulfur removal, dewatering and other trace element removal through a double desulfurization bed, a drying bed, and an adsorption bed of the purification unit and finally the carbon dioxide is purified to 99.9% purity; and the purified carbon dioxide is stored in the carbon dioxide tank;

the decarbonization aqueous solution for decarbonization uses MEA, DEA and AEEA mainly as the main absorbent, MDEA as the auxiliary absorption, composed of a plurality of active components with strong absorption ability, a preservative and a corrosion inhibitor, although each component has advantages, the disadvantage is that the average decarburization is generally low, the regeneration energy consumption is high, the solvent circulation rate is high; and the equipment is severely corroded; (ethanolamine, diethanolamine, hydroxyethylethylenediamine, methyldiethanolamine).

The invention adopts a composite decarbonization aqueous solution comprising a main absorption component, an auxiliary absorption component, an activation component, a corrosion inhibitor, an antioxidant and water; wherein the main absorption component comprise hydroxyethylethylenediamine AEEA, and the auxiliary absorption includes 2-amino-2-methyl-1-propanol AMP, MDEA and triethanolamine TEA, the active components comprise MEA, DEA and piperazine PZ, the corrosion inhibitor includes sodium citrate, and the antioxidants include sodium sulfite and copper acetate; the decarbonization aqueous solution has the advantages of large absorption capacity, high purification degree, high desorption rate and low regeneration energy consumption; and is suitable for using in the mixture gas with 3%-70% carbon dioxide from the flue gas.

The formula: mass fraction of hydroxyethylethylenediamine is 5%-35%; mass fraction of additive is 5%-30%; mass fraction of activated component is 1%-10%; mass fraction of corrosion inhibitor is 0.05%-1.0%; mass fraction of antioxidant content is 0.05%-1.0%; mass fraction of total butylamine is 35%-55%; mass fraction of water is 45%-65%.

The active component solute of the decarbonized aqueous solution is generally within 30%, and the remaining 70% solvent is water, and the solution that absorbs $CO_2$ (commonly known as the rich liquid) needs to be heated to a temperature of 100° C.-120° C. during the regeneration process, with the decomposition of the absorption intermediate at the temperature mentioned above, a large amount water will evaporate to result in excessive regeneration energy consumption; and the evaporated water needs to be condensed at the top of the regeneration tower to maintain the water balance in the system, the amount of condensed water required for the condensation process is large, so the cost of the decarbonized aqueous solution has been high, and the economic benefits cannot be optimized.

Preferably, the present invention also adopts a non-aqueous decarburization solution: N-ethylethanolamine is the solute; N,N-diethylethanolamine is the solvent; the weight percent of the solute in the non-aqueous decarburization solution is in the range of 20-80 wt %, and the rest is the solvent; the non-aqueous decarburization solution is used under the conditions of a pressure range of 0-1.2 MPa and in the temperature range of 10-140° C.; the solvent can also be used as a reactant in the process to increase the absorption, the desorption rate and desorption rate at the same time.

C. The Water Recovery Unit the water recovery unit uses a double-pipe water and heat recovery device to recover water and residual heat from the flue gas; the residual heat is used for heat pump power generation or steam turbine power generation, and the water is transferred and stored in the water tank for electrolytic hydrogen production or process water; wherein the double-pipe water and heat recovery device can respectively applied to the flue gas source, the combined decontamination and dust removal unit, the capture subsystem, the conversion subsystem, the utilization subsystem, and the energy source subsystem of the flue gas total recycling system, in the subsystem, dual-pipe water and heat recovery devices with various specifications are respectively produced according to the design principle of the double-pipe water and heat recovery device and the real function of the each subsystem and unit, respectively applied to each subsystem and unit of the flue gas total recycling system;

the double-pipe water and heat recovery device, as shown in the schematic diagram, relates to condensed water recovery, high-temperature heat or waste heat recovery, and waste water and waste residue treatment; the condensed water is transferred and stored in the water tank for use standby, high-temperature heat or residual heat is used for steam turbine power generation or heat pump power generation, it can also be used for the flue gas total recycling system heating or external heating.

The double-tube water and heat recovery device uses double heat pipe technology to recover heat or residual heat from the flue gas, it uses double refrigerant technology to recover gaseous water from the flue gas, efficiency of the integrated design of the water and residual heat recovery is high, and it is convenient for the subsequent process to comprehensively utilize water and residual heat.

D. Hydrogen Production Unit the hydrogen production unit adopts the electrolysis method to produce hydrogen and oxygen gas by using water captured by the water recovery unit; a water gas unit uses oxygen which is the production of the hydrogen production unit as comburent to burn the water gas to generate power, the power generated by the water gas unit is provided to the flue gas total recycling system; the high-purity hydrogen produced by the water gas unit and the hydrogen produced by the hydrogen-production unit are stored in the hydrogen tank together; for the non-water-gas power plant, the present invention uses integrated water gas system as a combined facilities of energy, hydrogen and oxygen of the total recycling system.

E. The Conversion Subsystem the conversion subsystem utilizes hydrogen produced by the hydrogen production unit or/and the water gas unit to carry out heterogeneous chemical reaction of the catalyst, hydrogen, carbon dioxide and a solid catalyst under the catalysis of a copper-based nano catalyst; a fixed-bed reactor is used as a catalytic reactor and a microplate reactor as a synthesis reactor placed bef. and aft., carbon dioxide is converted into methanol and a glycol by selective hydrogenation of cyclic carbonate intermediate;

1. conversion technology scheme: $CO_2$ is converted into methanol by catalytic hydrogenation, by using heterogeneous catalytic reaction system, wherein there are many kinds of copper-based catalyst carriers, and characteristics of the nano catalyst are high specific surface area, high dispersion, good thermal stability and high surface energy, and the surface active sites, the conversion rate of converting $CO_2$ into methanol and glycol by selective hydrogenation of cyclic carbonate intermediate and cyclic carbonate is up to 100%, the selectivity of methanol is up to 99%, the selectivity of glycol is in the range of 95-99%, the copper-based catalyst can be stably recycled after being filtered or centrifuged;

the processes of conversion of carbon dioxide to methanol and glycol at the same time by selective hydrogenation of cyclic carbonate intermediate are:

using a supported catalyst having a non-noble metal Cu as an active component with good hydrogenation activity, selectivity and stability to cyclic carbonate under mild conditions; wherein cyclic carbonate is a compound having at least three carbon atoms cyclic ring structure, having a chemical structural formula of:

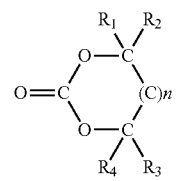

wherein each R1, R2, R3, R4, is independently selected from hydrogen, C1-12 alkyl, and optionally substituted aromatic ring, n is 0 or 1;

the concentration of the cyclic carbonate reaction solution is in the range of 10-100%, and the solvent of the cyclic carbonate reaction solution is selected from tetrahydrofuran or 1,4-dioxane;

$CO_2$+ethylene oxide–ethylene carbonate

Ethylene carbonate+$H_2$–methanol+ethylene glyco+ethylene oxide wherein the reaction condition is mild, the process is the green reaction with high efficiency, the catalyst preparation process is simple, the production cost is low, the catalytic performance is stable, and the production processes of industrialization is easy;

wherein the addition reaction of ethylene oxide and carbon dioxide for preparing ethylene carbonate is an exothermic and volume-reducing reaction. From the aspect of chemical equilibrium, the conditions of low temperature and high pressure are favorable for the reaction, and the copper-based nano catalyst is selected to make the reaction proceed smoothly, the system is a heterogeneous catalytic system;

wherein ethylene carbonate (EC) is an excellent organic solvent that can dissolve a variety of polymers; it can be used as an organic intermediate to replace ethylene oxide in dioxylation reaction; and it is a main material for the production of dimethyl carbonate by transesterification; the transesterification method is a method for preparing ethylene carbonate by transesterification of diethyl carbonate and ethylene glycol, and the process is not complicated and the key point is to apply a suitable catalyst to increase the reaction temperature of the system, and speed up the reaction.

2. conversion reactor configuration: the catalytic reactor is the fixed bed reactor, the synthesis reactor is the microplate reactor, and the catalytic reactor and the synthesis reactor are double-loop circulating structure, a copper boron nano catalyst is used in the fixed bed reactor, a copper plate nano catalyst is used in the microplate reactor; wherein the hydrogen and carbon dioxide gas sent to the fixed bed reactor through a heat exchanger by a transfer pump react with the ethylene oxide in the liquid phase to form the ethylene carbonate intermediate, under the catalyzed reaction of the copper boron nano catalyst, the methanol and glycol are produced in hydrogen reduction reaction; wherein after transferring heat by passing through the heat exchanger and cooling down by a condenser, the reaction gas is sent to a gas-liquid separator to separate into the gas and liquid, the gas is sent the microplate reactor, the liquid is transferred and stored in an alcohol tank; wherein in the microplate reactor, the gas and the ethylene carbonate in the liquid phase react with hydrogen under the catalyzed reaction of the copper ruthenium nano catalyst to produce methanol and glycol; after passing through the heat exchanger and the condenser, the reaction mixture is sent to a gas-liquid separator, and the liquid phase product is transferred and stored in a glycol tank, the gas phase product is returned back and cyclically reacted with hydrogen and carbon dioxide gas;

a stirring reaction accelerator is respectively disposed at the top of the catalytic reactor and the synthesis reactor.

3. Heterogeneous Catalytic System:

(1) Liquid phase: the solvent is tetrahydrofuran or 1,4-dioxane; the solute is ethylene oxide and ethylene carbonate;

(2) Solid phase: silica-supported copper-nano catalysts is used, copper boron nano catalysts is used in the fixed bed reactor; copper plated nano catalysts is used in the microplate reactor;

(3) Gas phase: hydrogen, carbon dioxide gas, reaction cycle mixed gas;

4. System Composition and Ratio:

The supported copper catalyst is used for hydrogenation of cyclic carbonate to make methanol and glycol, the composition of catalyst is Cu/X or Cu-M/X, wherein the carrier X is any one or two of the composites of $SiO_2$, $Al_2O_3$, MgO, $ZrO_2$, ZnO, the auxiliary agent M is any one or more metal selected from Ba, Mn, Y, La, Ce, Sm, Ga, B, and the Cu metal-loading in the catalyst is 5-70.%, preferably 10-60%, the loading of the auxiliary agent M in the catalyst is 0.0-15% oxide, preferably 0.1-12% oxide, and the balance is an oxide carrier; the reaction temperature is 120-180° C., the hydrogen pressure is 2-8 MPa, the reaction time is 4-20 h;

Cu metal-loading in the catalyst is preferably 10-60%, the loading of the auxiliary agent M in the catalyst is preferably 0.1-12% oxide, and the balance is an oxide carrier.

5. Reaction conditions: reaction temperature is 120-180° C., hydrogen pressure is 2-8 MPa, reaction time is 4-20 h.

6. Preparation of active copper-based nano catalyst: the catalyst precursor is prepared by a conventional co-precipitation method or a deposition precipitation method, and the catalyst precursor is dried at 80-120° C. for 10-13 hours, and calcined at 300-600° C. for 3-8 hours; Boron additives and ink are soluble salts, specifically selected from nitrate or acetate, non-metal B is selected from boric acid or boron oxide, co-precipitated with copper salt, copper nitrate or copper acetate, or based on Cu/X auxiliary catalyst precursor added by the upper volume impregnation method; activation of the catalyst precursor: at 250-500° C., reduction in hydrogen atmosphere for 2-6 h to obtain an active catalyst;

(1) Preparation of Copper Boron Catalyst: (43% Cu—$B_2O_3$/$SiO_2$)

Preparation of the precursor: Take 15.00 g of copper nitrate trihydrate and 25.00 g of 20% by mass of acidic silica sol into a round bottom flask, 1.25 mL of distilled water is added thereto to stir and disperse, precipitated with 10 wt % NaOH solution used as precipitant at pH≥10, then the temperature was raised to 80° C. for 4 h. After cooling and suction filtration, the pre-precursor is washed with distilled water until neutral PH and dried at 120° C. for 12 h, then crushed and sieved into nano-powder, thus the precursor is obtained;

Catalyst preparation: The precursor was impregnated with 3% $B_2$ $O_3$ auxiliary agent by mass, described as follows: the 0.26 g of boric acid was weighed to add to a certain amount of distilled water to prepare a solution, and 4.90 g of the precursor was impregnated in an equal volume, and dried at 120° C. for 12 h, calcined at 500° C. for 3 hours in a muffle furnace, reduced and activated at 400° C. for 3 h in a hydrogen atmosphere, thus an active catalyst of 43% Cu—$B_2$ $O_3$/$SiO_2$ was obtained.

(2) Preparation of Copper Ruthenium Catalyst: (43% Cu—$La_2$ $O_3$/$SiO_2$)

Preparation of the precursor: Take 15.00 g of copper nitrate trihydrate, 25.00 g of of acidic silica sol with 25% by mass into a round bottom flask, add 125 mL of distilled water to stir, disperse and dissolve thereof, precipitate with 10 wt % NaOH solution which is used as precipitant until the pH≥10 and the temperature was raised to 80° C. for 4 h. After cooling and suction filtration, washing with distilled water to neutrality, drying at 120° C. for 12 h, grinding and sieving into nano-parts to obtain the precursor;

Catalyst preparation: The precursor was impregnated with $La_2O_3$ auxiliary agent with a mass fraction of 3%, as follows: 0.42 g of lanthanum nitrate hexahydrate was weighed, a certain amount of distilled water was added to prepare a solution, and an equal volume of 4.90 g of the precursor was impregnated at 120° C. After drying for 12 h, calcination at 500° C. for 3 h in a muffle furnace, and reduction and activation at 400° C. for 3 h in a hydrogen atmosphere, the active catalyst 43% Cu—$La_2$ $O_3$/$SiO_2$ was obtained.

F. The Utilization Subsystem

The utilization subsystem comprises the supercritical refining and the preparation of nanocellulose unit, a supercritical carbon dioxide nanocellulose foaming material unit;

(1) the supercritical refining and preparation of nanocellulose unit comprises cellulose and a refining device;

wherein the particle size of the cellulose is in micrometer level, and the cellulose comprises any one or more of wood fiber, carbon or carbon fiber, silicon or silicon fiber, metal or metal fiber, and graphite or graphite fiber;

wherein the refining device is a fully sealed, high pressure resistant, waterless device, the cellulose is mixed with a supercritical carbon dioxide liquid by the refining device, and a refiner is used to grind micron-sized cellulose into nano-sized fibers, the nano-scale cellulose and supercritical carbon dioxide constitute a supercritical carbon dioxide nanocellulose slurry, referred to as a nano-slurry; wherein the amount of the nano-slurry content of the nano-slurry is greater than 1%;

wherein the refining device comprises a slurry tank, a refiner and a conveyor; wherein the slurry tank, the refiner and the conveyor are connected in a sealed mariner through a three-way valve, a vacuum valve and a high pressure pipeline, and operated under supercritical conditions, the internal circulation flow is filled with a slurry composed of liquid-phase supercritical carbon dioxide where the cellulose powder dissolved; the conveyor is equipped with a pump motor and a fluid pump in a chassis, wherein the pump motor drives the fluid pump through a drive belt, sucks the slurry from the slurry tank to the pump inlet, and delivers the slurry from the pump outlet to a refiner feed port through the high pressure pipeline, the slurry is conveyed to a place between a fixed grinding disc and a rotating grinding disc through a side flow passage, after finely ground and the slurry is introduced into a material cylinder by a hollow rotating shaft, and is sent to the slurry tank through a outlet and the high pressure pipeline, thus the slurry is formed into a circulating transport flow in a supercritical state.

A chassis is arranged on the lower shaft of the refiner, and the hollow rotating shaft driven by a grinding motor through a drive belt is displaced inside the chassis, and the hollow rotating shaft drives the rotating grinding disc to rotate at a high speed, and the superfine nano-grinding gears meshed with each other are arranged on the rotating grinding disc and the fixed grinding disc the fixed grinding disc, the micron scale cellulose is grinded into nanoscale cellulose by the superfine nano-grinding gears.

The slurry tank is equipped with a temperature sensor, a pressure sensor, a density sensor and a particle size detecting sensor for detecting the temperature, pressure, density and cellulose particle size of the slurry in the slurry tank, respectively, and the detected parameter information is displayed by the PLC controller.

A heater and a cooler are disposed outside the slurry tank for controlling the temperature of the slurry in the supercritical state in the slurry tank.

A $CO_2$ liquid inlet on the slurry tank is used to feed the supercritical carbon dioxide liquid, and the pressure of the supercritical carbon dioxide is controlled by releasing or adding a carbon dioxide liquid controlled by the valve group and the vacuum valve disposed on the $CO_2$ liquid inlet.

The slurry tank further includes a mixer, a stirrer, a cleaning tank, a outlet, a cleaning agent and a sewage outlet; the mixer and the stirrer are used for mixing and stirring the slurry in the slurry tank, and the cleaning tank is filled with the cleaning agent for cleaning the refining device, and the sewage outlet is for discharging the cleaning waste liquid.

The refiner further includes a grinding body, a pressure gauge, a flow meter, the grinding body is a housing of the refiner, and the pressure gauge and the flow meter are assembled on the high pressure pipeline of the outlet for displaying the pressure and flow rate of the supercritical slurry.

(2) The supercritical carbon dioxide nanocellulose foaming material unit comprises an auxiliary device, a compounding device, an injection device, a twin-screw extruder, a foaming device, and a foaming material;

wherein the compounding device adjusts the ratio of supercritical carbon dioxide and nanocellulose in the nano slurry, and releases carbon dioxide therein to increase the content of nanocellulose in the nano slurry, after releasing the carbon dioxide through the compounding device. The ratio of carbon dioxide to nanocellulose in the nanoslurry is (30%-70%): (70%-30%) (wt %) to keep certain amount of nanocellulose in the foaming material, and improve the performance thereof; the compounding device is connected with a nano-slurry storage tank, and the nano-slurry storage tank is used for storing and supplying the made nano-slurry;

wherein the amount of carbon dioxide dissolved in the foaming material is positively correlated with the pressure of supercritical carbon dioxide; when the pressure is 5 MPa, the amount of dissolved carbon dioxide is 3%; when the pressure is 15 MPa, the amount of dissolved carbon dioxide is 10%. The pressure of present invention is about 20 MPa in order to increase the amount of dissolved carbon dioxide to a higher percentage;

wherein the utilization system mixes the adjusted nano-slurry, supercritical carbon dioxide, and accelerator to a design formula, and uniformly mixes to obtain the supercritical liquid material by a high-pressure mixer; further, the supercritical liquid material is injected into the twin-screw extruder at a high pressure through the nanometer cellulose injection device; and the particles material are fed into the twin-screw extruder at the same time, then the supercritical liquid material is melt-mixed with thereof, and extruded through a mold to obtain an extruded product. The extruded product is foamed by a foaming process to obtain a foam material product;

wherein the auxiliary device is equipped with a supercritical carbon dioxide tank supplying a required supercritical carbon dioxide liquid, a CO2 pressure stabilizer, a high pressure pump, a CO2 thermostat and a mass flow meter for quantitative measurement of providing the requited supercritical carbon dioxide; the high pressure pump and a mass flow is used for quantitative measurement of providing accelerating agent;

wherein the material particles include plastic particles or powders, cement particles or powders, glass particles or powders; the foaming materials include foamed plastics, foamed cement, foamed glass, and the foamed materials include sheets, plate, profile, block or structure.

The performance index of the foaming material is: (taking PP foam material as an example).

1. the content of nanocellulose is: 1%-5%;
2. the modulus of elasticity is: 3 GPa-10 GPa;
3. the heat distortion temperature (HDT) is: 130° C.-150° C.;
4. the intensity is: 1000 KPa-3000 KPa.

In the prior art, the strength of the related domestic foam product only is 150 KPa-500 KPa; the strength of the related foam product in the United States only is 1000 KPa.

G. The Energy Subsystem

The energy subsystem is used to comprehensively regulate and configure the power consumption and heat distribution and recovery of each subsystem, and the purpose is to satisfy the electricity and heat consumptions of each subsystem by fully using electricity or heat from clean energy power generation, hydrogen power generation, waste heat recovery and power generation, and the self-sufficiency of the entire total recycling system is finally realized;

therefore, the energy subsystem is equipped with the solar power generation device and the wind power generation device, and storing energy by electrolyzing water to make hydrogen, and when the power generated by solar power generation and wind power generation is rich, the excess energy is stored in the form of electrolytic hydrogen; when the system needs additional power, the needed power can be provided by the gas generator through burning the hydrogencan gas.

The system makes full use of the residual heat of each subsystem by heat pump and waste heat recovery technology, and the excess heat is stored in the form of supercritical carbon dioxide, and the stored heat energy can be used by releasing heat through the supercritical carbon dioxide when needed.

The energy subsystem further comprises high-purity oxygen generated when water is electrolyzed, and the electrolytic oxygen is used for coal-fired power generation of a water gas power plant, and at the same time, high-purity hydrogen after combustion of the water gas power plant is obtained, by storing or using the obtained hydrogen in the conversion subsystem, the whole system is operated in a comprehensive cycle and comprehensive resource mode; through the capture, conversion and utilization of carbon dioxide, the final output is methanol, glycol, foams, which constitutes the material balance of the system; the integration of the energy system enables the utilization of clean energy, hydrogen energy and system heat energy to achieve self-sufficiency in energy consumption of the entire system, and also output part of heat energy, electric energy or hydrogen energy. Thereby full quantification of energy utilization and full quantification of flue gas utilization are achieved The energy subsystem uses solar energy and wind energy without carbon dioxide emissions, in the initial stage of the total resource system, it is still necessary to use market-oriented electric energy and heat energy as the initial system starting energy.

The beneficial effects of the present technology described above are: the flue gas total recycling system of the present invention can directly collect and convert high-concentration carbon dioxide in the flue gas, the carbon dioxide emission source, the collection and purified rate reaches 95%; the collected carbon dioxide is reacted with high-efficiency non-precious metal nano catalyst to form methanol and glycol at a temperature slightly higher than the exhaust gas of the flue gas, and the conversion rate and selectivity are both above 90%. In proportion, some of the collected carbon dioxide is converted into a supercritical state, and nanofiber materials are efficiently prepared to produce a variety of microscopic foaming building materials, the density of the microscopic polymer composite foam building material can be reduced to 30 kg/m$^3$ (the density of the non-foamed material is 1400 kg/m$^3$) to improve the performance of the building material; in the present invention, just converting 30% of the total carbon dioxide of the large thermal power station in China, the market size of its products can reach 11 trillion CNY.

For the first time, this invention fully utilizes carbon dioxide from the flue gas in a thermal power plant as a resource to produce considerable and sustainable economic value; this invention also collects and treats the flue gas from the thermal power station for the first time without directly discharging the combustion product to the air; therefore, the economic value of the present invention is sufficient to offset the cost of simultaneously treating sulfur dioxide and particulate matter to ensure the economic benefits of the thermal power plant, and completely solve the problem of haze.

Since the beginning of human civilization, the fossil energy that human beings depend on for survival and development has always brought energy, carbon dioxide, sulfur dioxide, nitrogen oxides and ash to the direct emission of various fuels to the atmosphere to accumulated more carbon dioxide in the atmosphere; the rapid development of human beings in the past 50 years has caused the global greenhouse effect and global warming recognized as facts. In 2014, the concentration of carbon dioxide in the Earth's atmosphere is reached 408 ppm, breaking the balance of that is 0.03% (300 ppm) on earth for 25 million years. For the first time, the present invention totally collects and treats the flue gas from the thermal power station or the chimney without directly discharging any combustion products into the atmosphere, the implementation of the present invention will contribute to reduce the concentration of carbon dioxide in the earth's atmosphere, and reduce or even completely eliminate the smog.

Although renewable energy such as solar energy and wind energy have been developed for many years, governments are also vigorously promoting it. However, due to the instability of power generation caused by climate change, it is difficult to access the grid of thermal power stations and the voltage regulation system is even several times larger than the renewable energy power station with no economy. Therefore, it is only in China that up to 60 billion NCY worth of wind power can't be netted and wasted. Most of the wind power stations are in underdeveloped areas in western China, while wind power produces hydrogen, and then transports hydrogen over long distances or establishes hydrogen transport pipelines, but hydrogen is the lightest gas, and its transportation cost is too high; further, hydrogen is very easy to explode. There has always been a view in the industry that these two clean energy sources have no future. The use of flue gas from thermal power stations, especially the conversion of carbon dioxide gas, must rely on energy sources other than the energy of the thermal power station to provide the required energy, so that coal and natural gas are burned to generate electricity, and other carbon dioxide in the flue gas of the thermal power station is converted by other renewable energy sources. In order to achieve carbon closed loop and absolute emission reduction; renewable energy and fossil energy complement each other, while providing electrical energy, air pollution problems, global greenhouse effect and other difficult problems may be completely solved.

BRIEF DESCRIPTION OF THE DRAWINGS

The technical in the embodiments of the present invention are clearly and completely described in the following with reference to the accompanying drawings. It is obvious that the described embodiments are only a part of the embodiments of the present invention, but not all embodiments. All other embodiments obtained by those skilled in the art based on the embodiments of the present invention without creative efforts are within the scope of the present invention.

Figure 1:
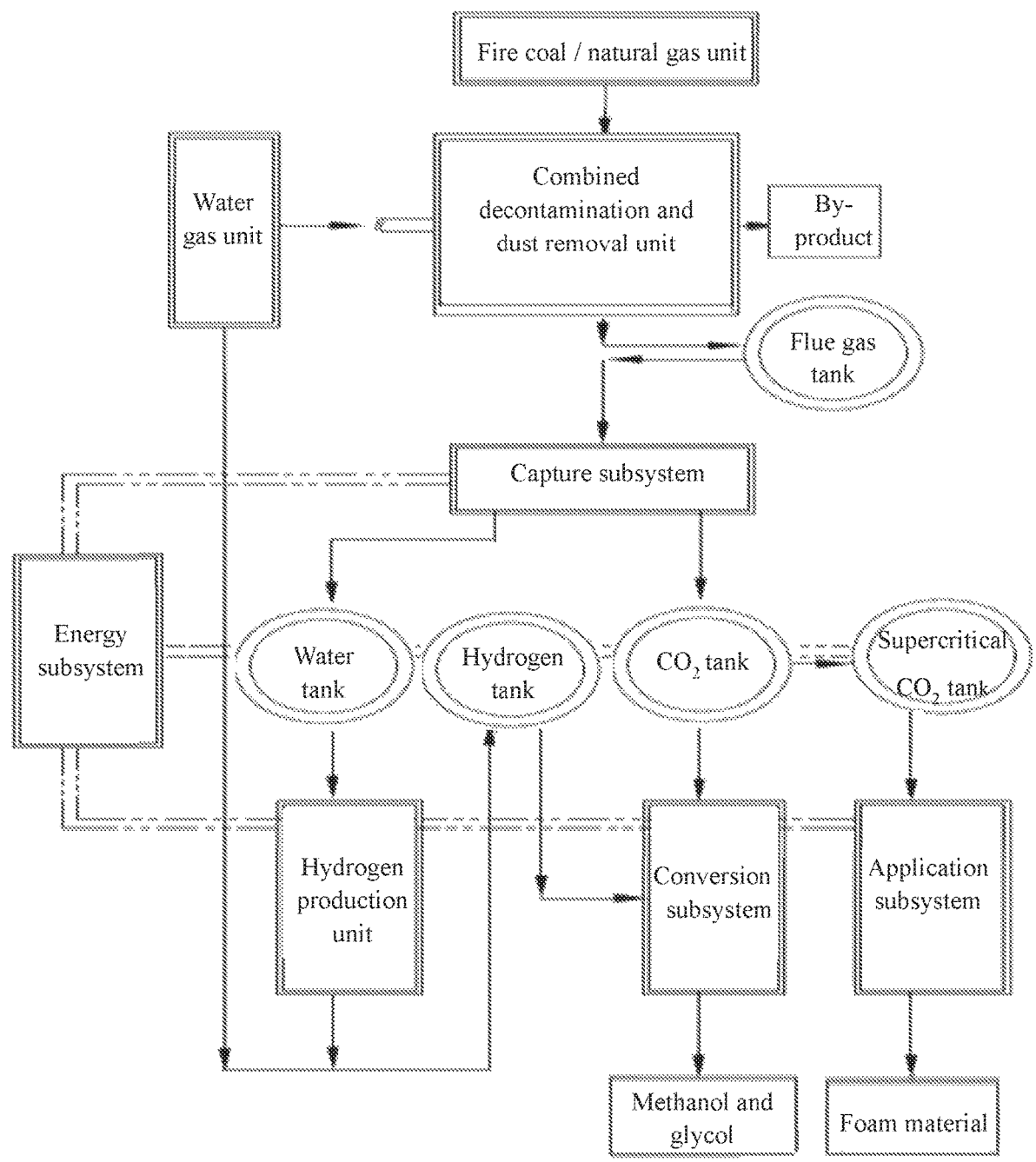
FIG. 1 illustrates schematic diagram of Example 1.

1. Desulfurization tower 2. Absorption tower 3. Regeneration tower 4. Heat exchanger 5. Absorbent tank 6. Gas-liquid separator 7. Transfer pump 8. Desulfurization bed 9. Drying bed 10. Adsorption bed 11. Condenser 12. Adsorption tower 13. Multi-stage dust collector 14. Magnetic separator 15. Regenerator 16. Stirring reaction accelerator 100. Slurry tank 101. Mixer 102. Stirrer 103. Heater 104. Temperature sensor 105. Powder feed port 106. $CO_2$ liquid inlet 107. Slurry 108. Cleaning tank 109. Three-way valve 110. Vacuum valve 111. Outlet 112. High pressure pipeline 113. Cleaning agent 114. Sewage outlet 200. Refiner 201. Grinding body 202. Grinding motor 203. Material cylinder 204. Feed port 205. Pressure gauge 206. Flow meter 207. Fixed grinding disc 208. Rotating grinding disc 209. Hollow rotating shaft 210. Side flow passage 211. Outlet 212. Drive belt 213. Chassis 300. Conveyor 301. Pump motor 302. Fluid pump 303. Pump inlet 304. Pump outlet 305. Drive belt 306. Chassis

DETAILED DESCRIPTION OF THE INVENTION

Technical solutions according to the embodiments of the present invention are hereinafter described clearly and completely in conjunction with the drawings of the embodiments of the present invention. Apparently, the described embodiments are only some of the embodiments of the present utilization but not all the embodiments. Any other embodiments obtained by those skilled in the art based on the embodiments of the present disclosure without any creative work fall within the scope of protection of the present invention.

Figure 2:
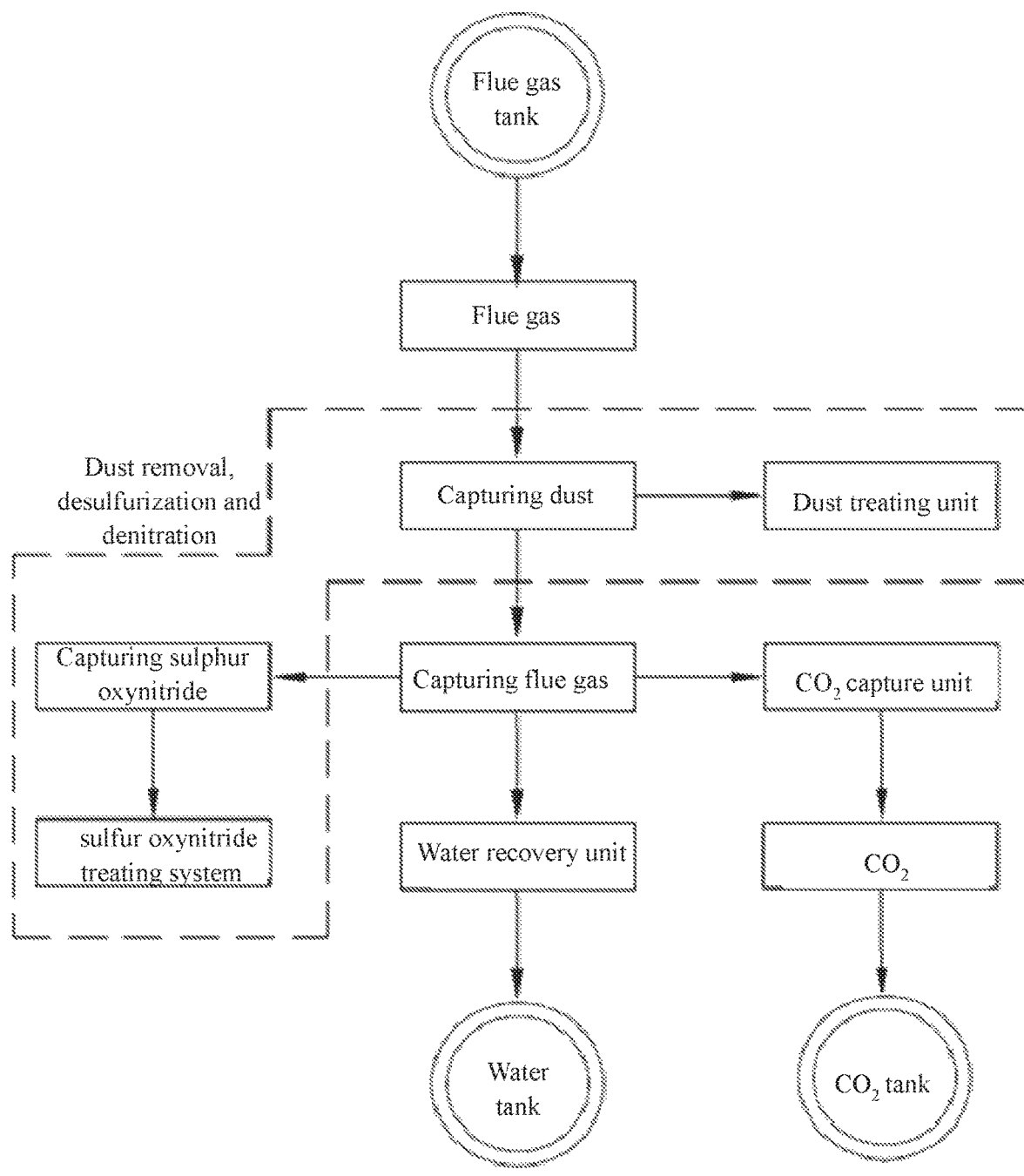
FIG. 2 illustrates schematic diagram of a capture subsystem of Example 1.
Figure 3:
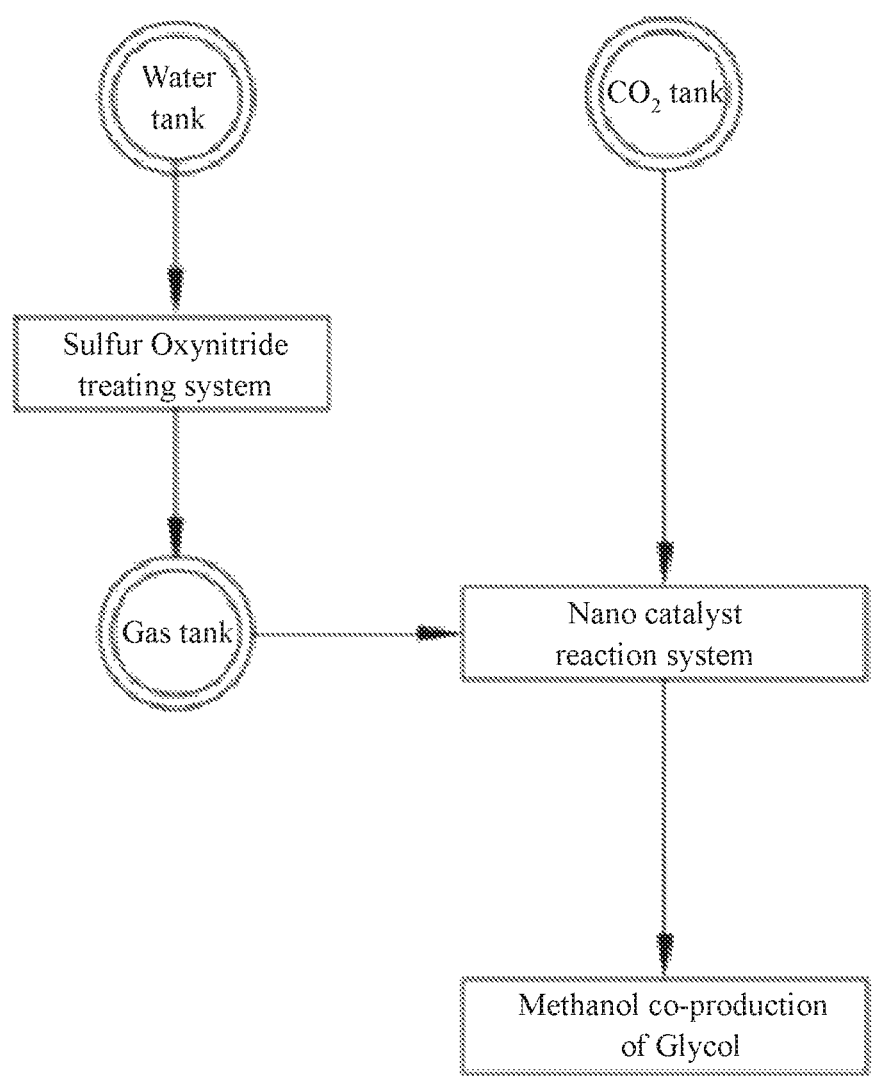
FIG. 3 illustrates schematic diagram of a conversion subsystem of Example 1.
Figure 4:
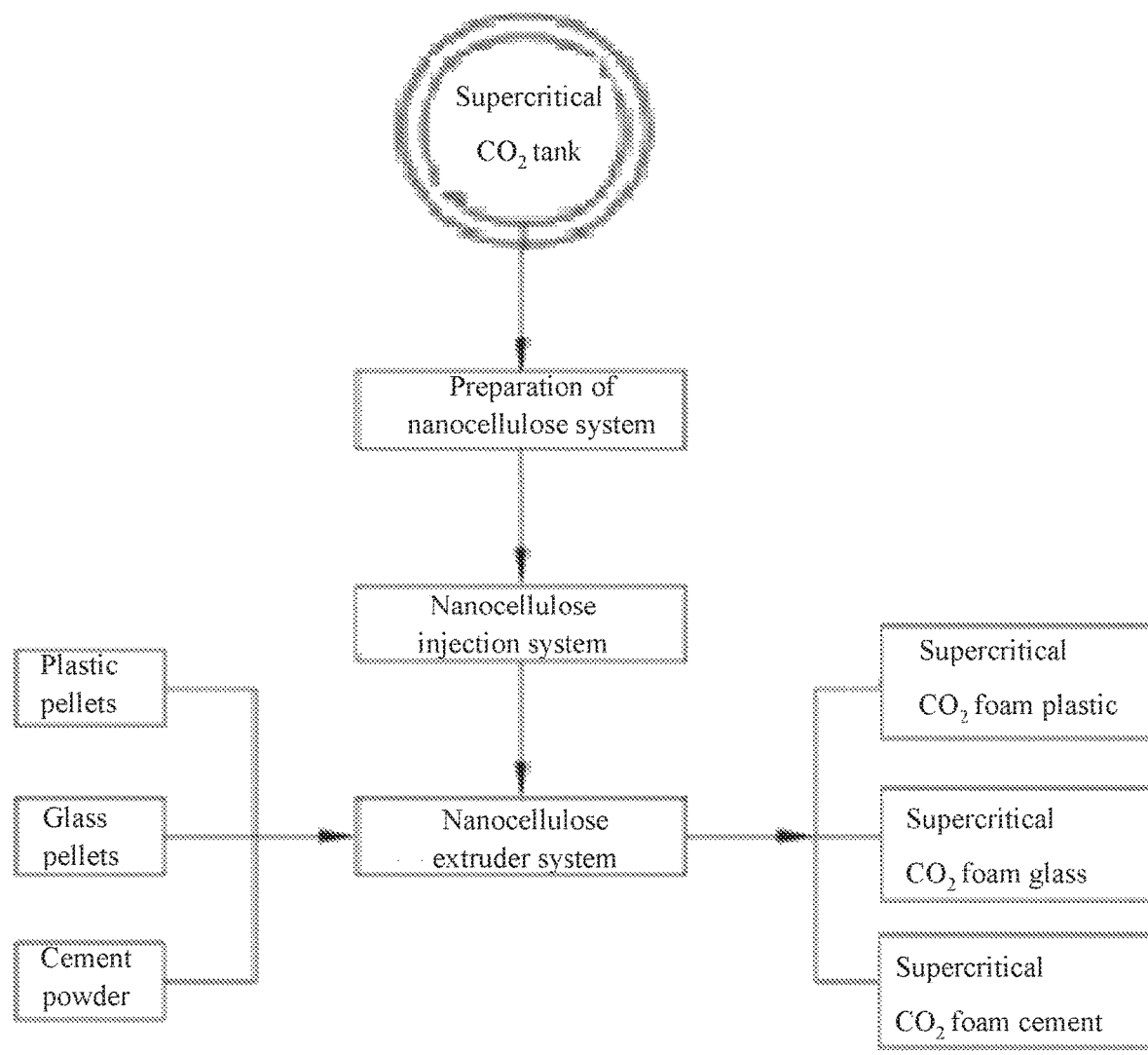
FIG. 4 illustrates schematic diagram of an utilization subsystem of Example 1.
Figure 5:
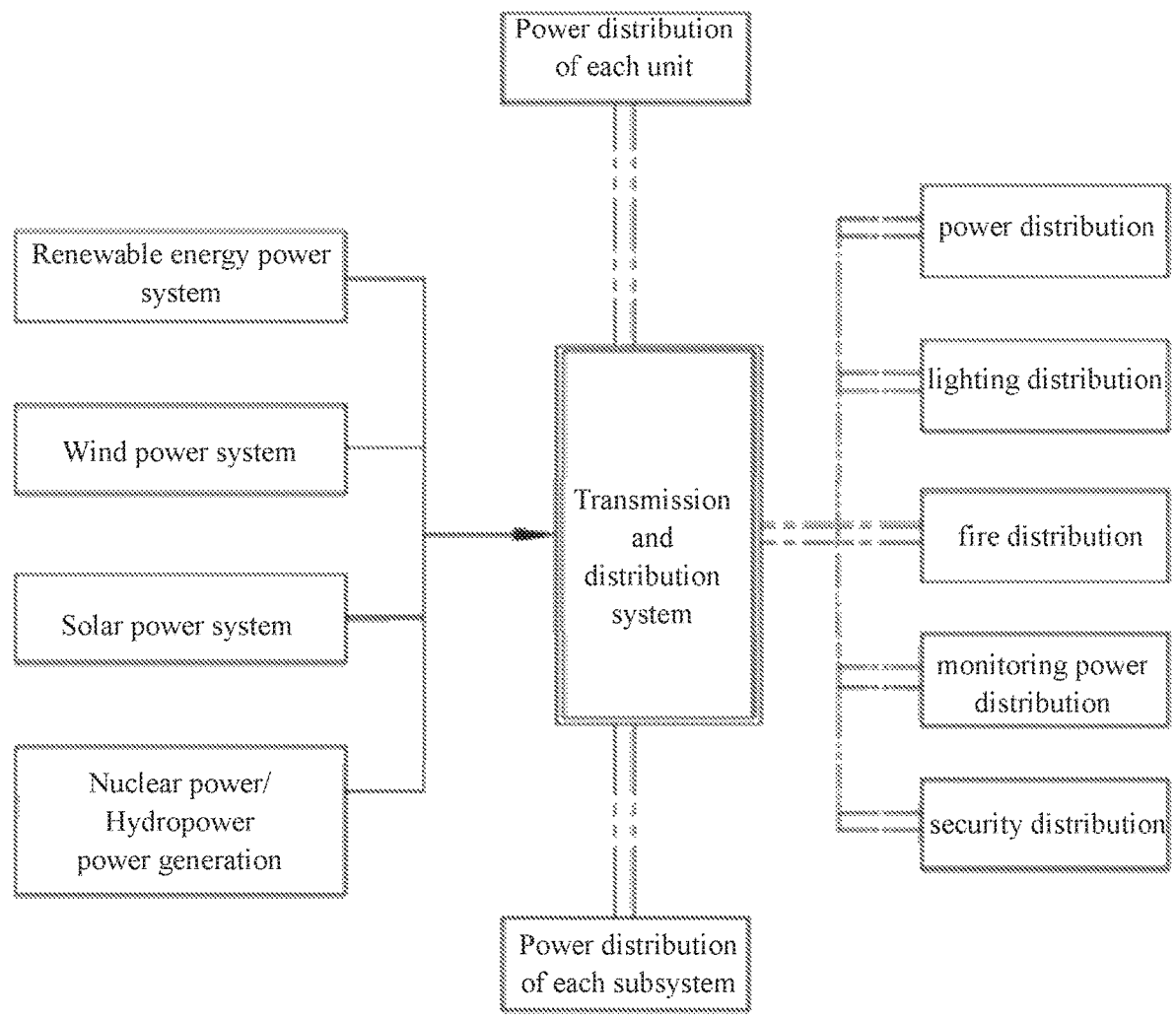
FIG. 5 illustrates schematic diagram of an energy subsystem of Example 1.
Figure 6:
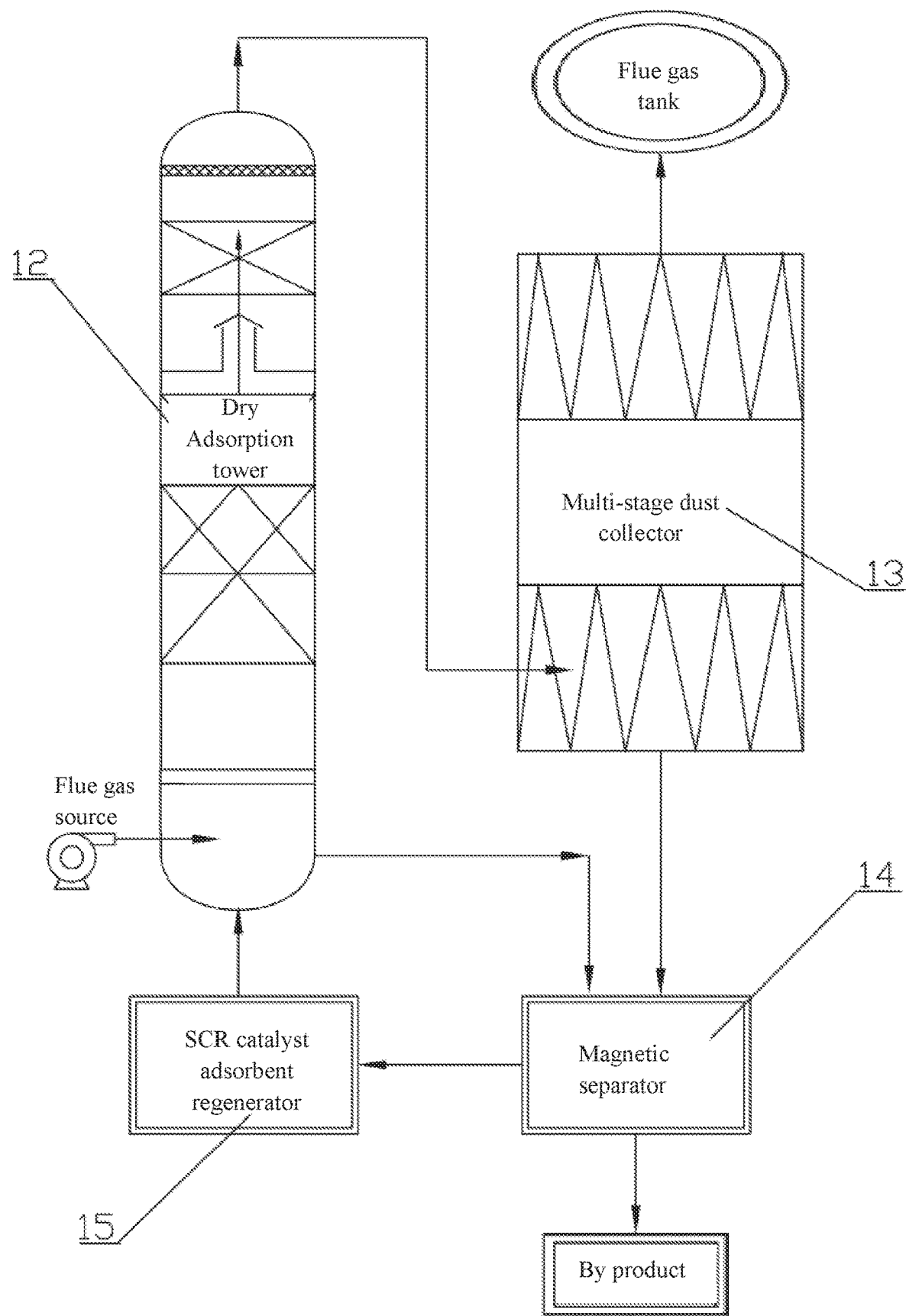
FIG. 6 illustrates schematic diagram of a combined decontamination and dust removal unit of Example 1.
Figure 7:
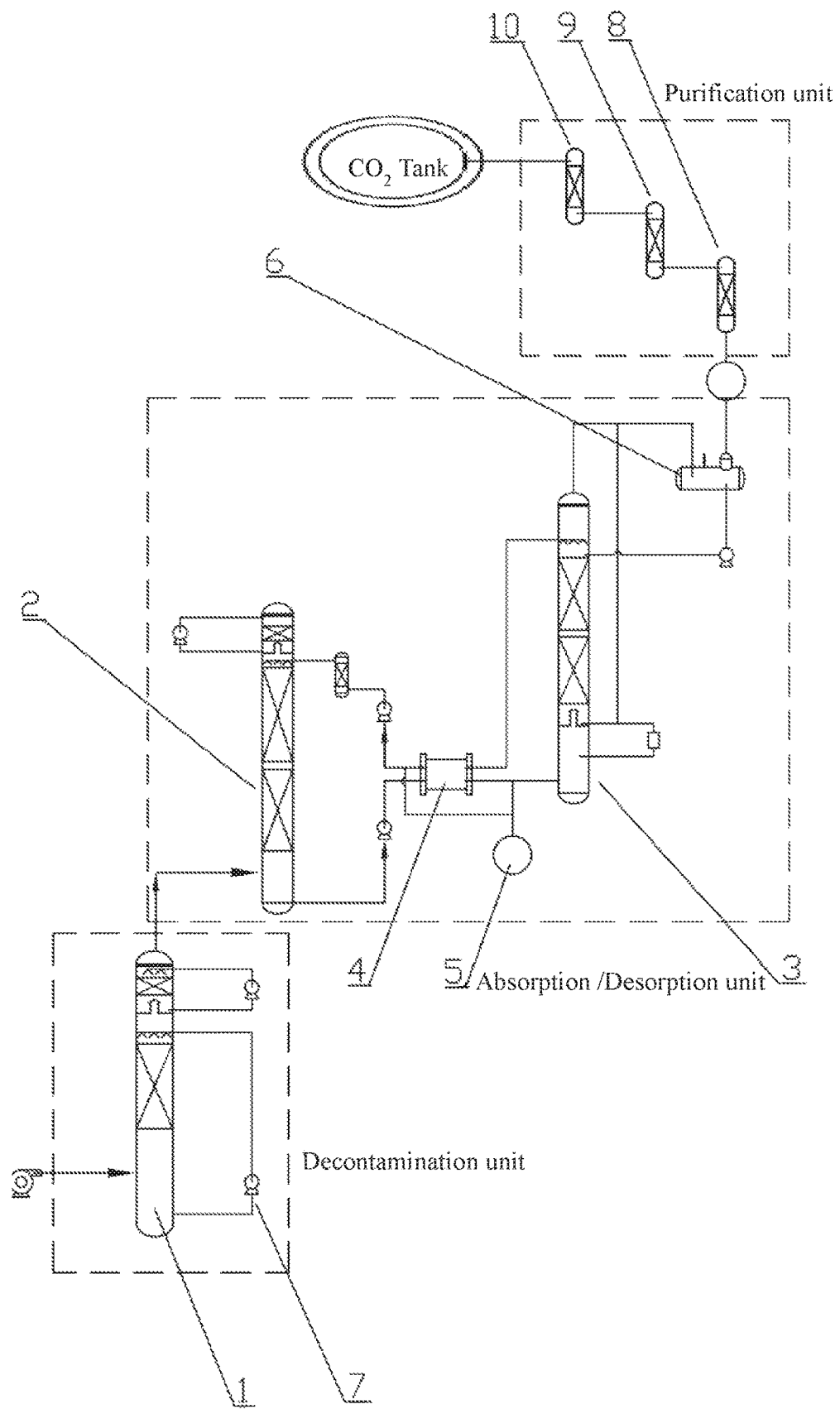
FIG. 7 illustrates schematic diagram of a capture subsystem of process.
Figure 8:
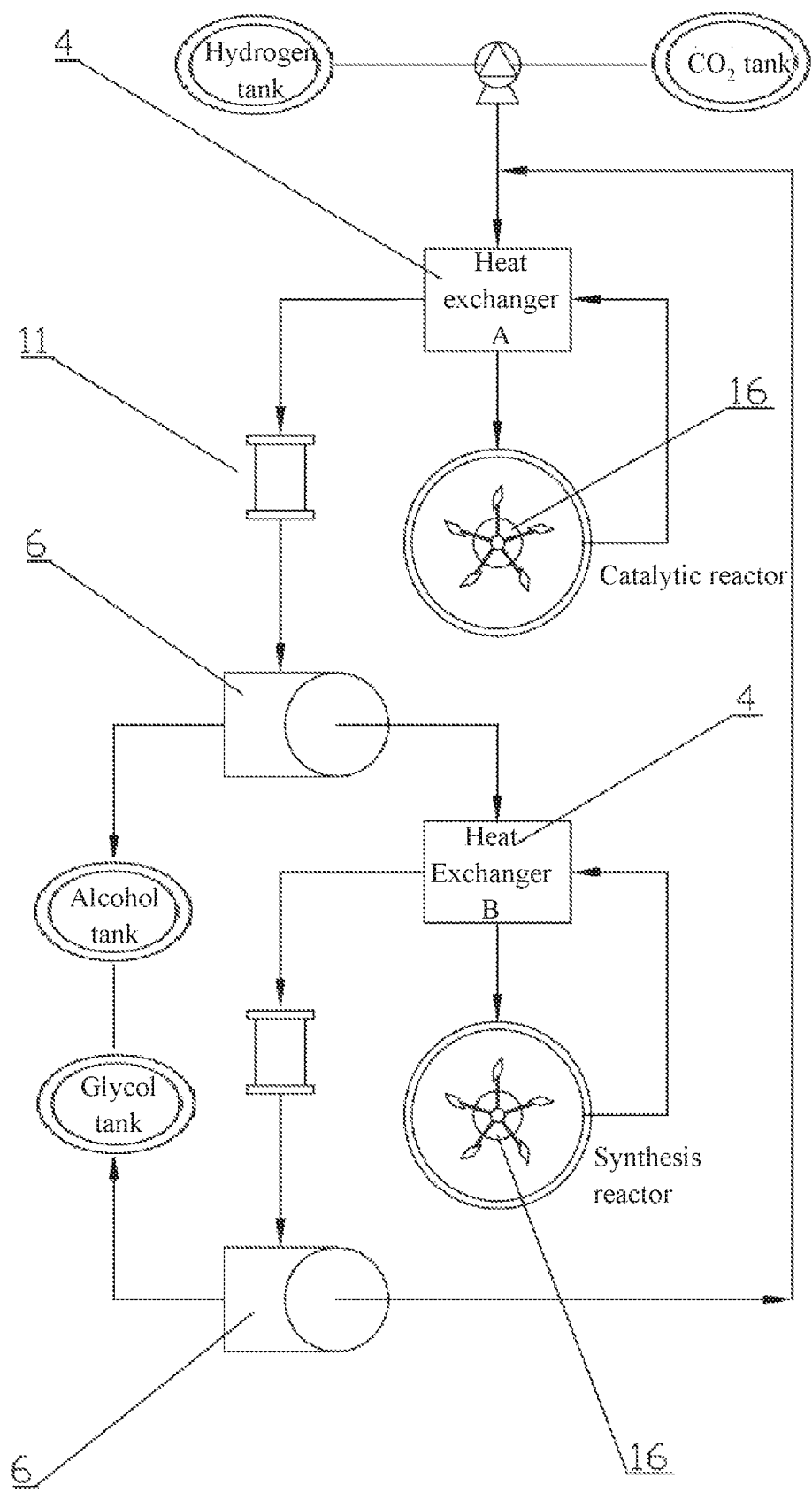
FIG. 8 illustrates schematic diagram of a conversion subsystem of process.
Figure 9:
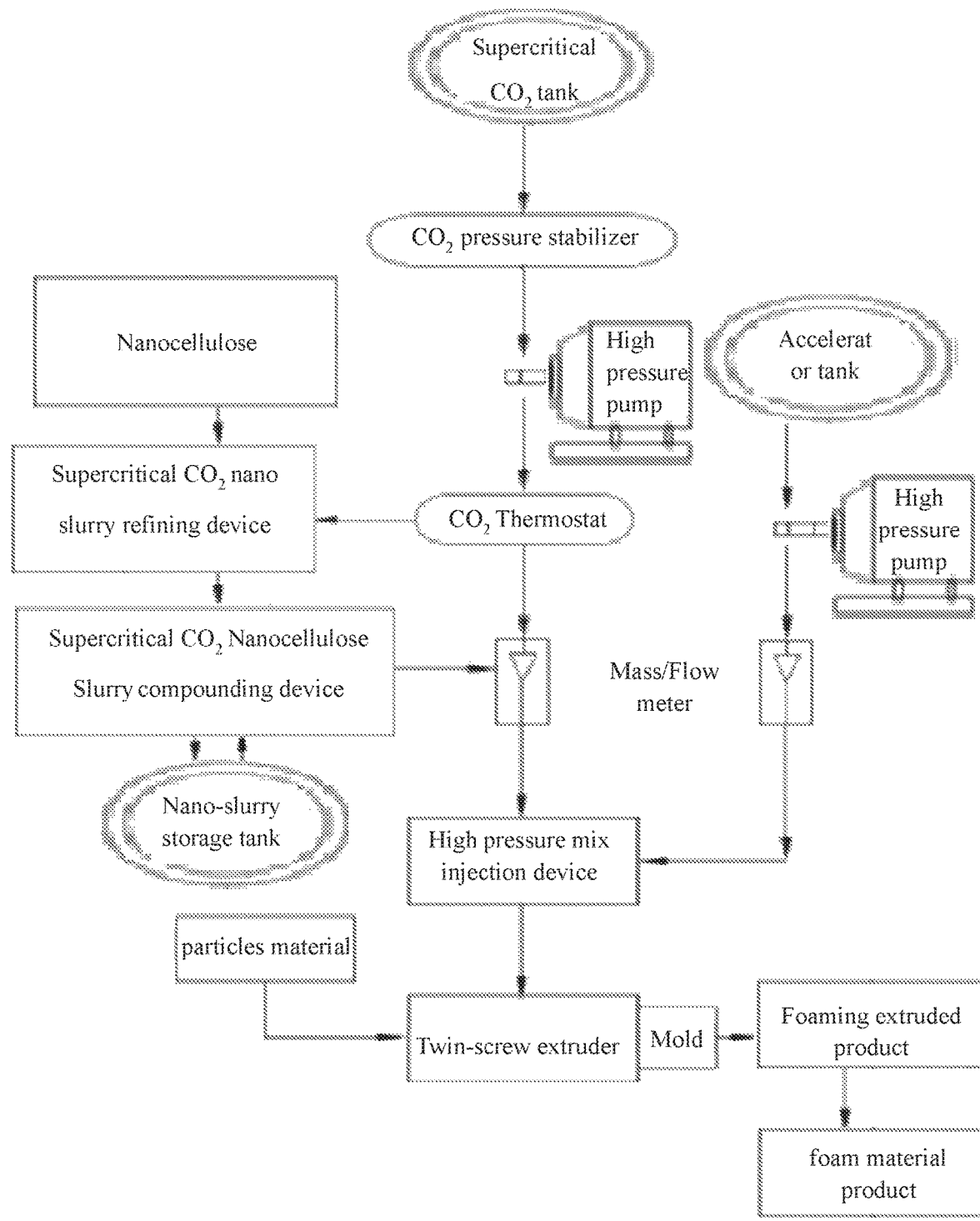
FIG. 9 illustrates schematic diagram of an utilization subsystem of process.
Figure 10:
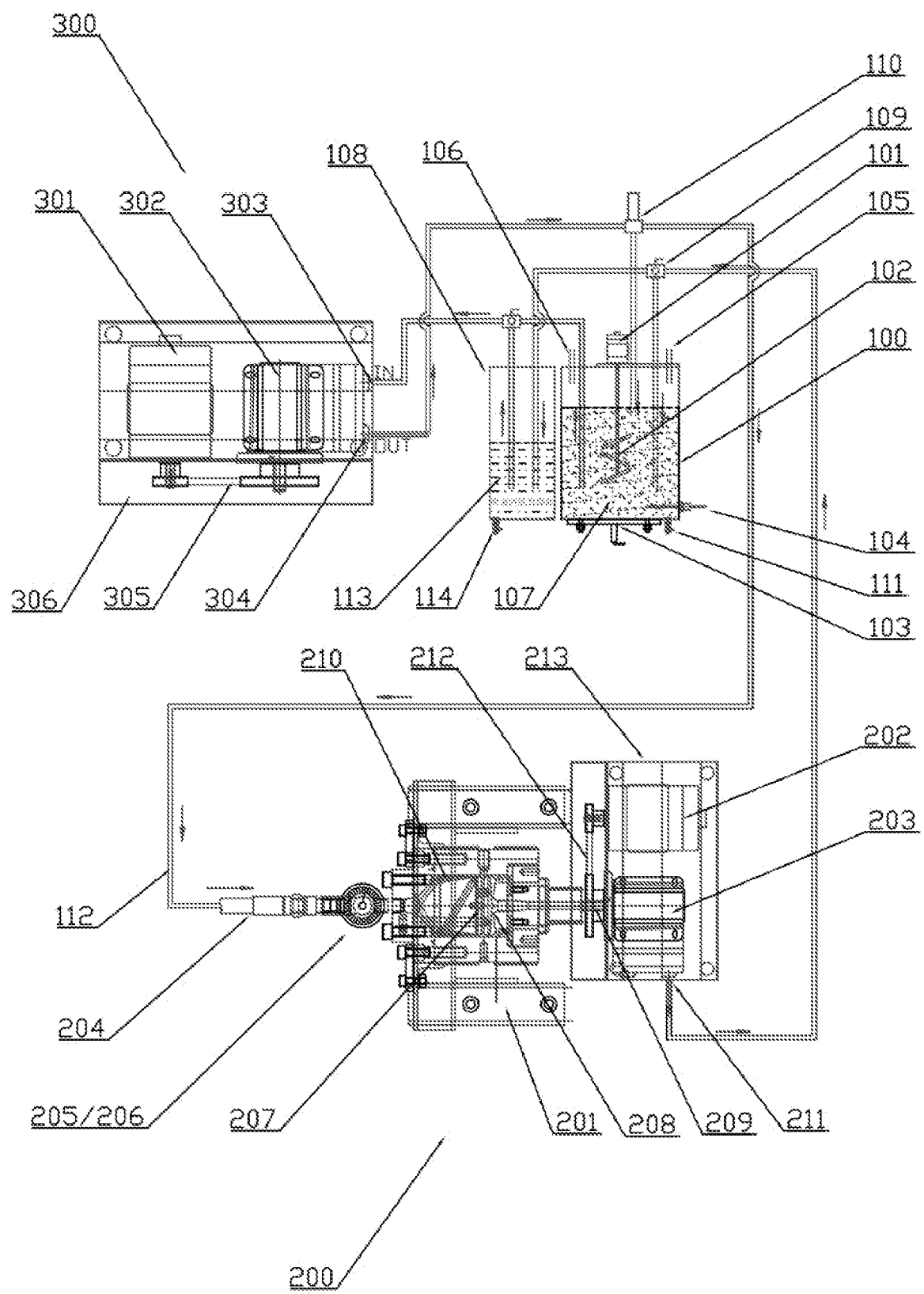
FIG. 10 illustrates schematic diagram of supercritical carbon dioxide nanocellulose foaming material unit of Example 1.

According to FIG. 1 to FIG. 10, the present invention provides a total recycling system of capturing, conversion and utilization of flue gas from factory, power plant and refinery, comprising a combined decontamination and dust removal unit, a hydrogen production unit, a capture subsystem, a conversion subsystem, an utilization subsystem, a water gas unit, a carbon dioxide capture unit, a water recovery unit, a supercritical refining and preparation of nanocellulose unit, a supercritical carbon dioxide nanocellulose foaming material unit.

wherein the flue gas includes dust particles, a gaseous compound, a trace element, carbon dioxide, and water vapor, wherein the gaseous compound includes at least nitrogen oxides and sulfur oxides; wherein the flue gas total recycling system removes the dust particles and the gaseous compound by the combined decontamination and dust removal unit; capturing carbon dioxide by the carbon dioxide capture unit in the capture subsystem and pressurizing the captured carbon dioxide to supercritical carbon dioxide; recovering water vapor in the flue gas by the water recovery unit; decomposing the recovered water into hydrogen and oxygen through the hydrogen production unit, and feeding the oxygen into the water gas unit for combustion support to further obtain a high-purity hydrogen through the water gas unit; reacting the captured carbon dioxide having high stability and low energy with the high-energy ethylene oxide molecule to form ethylene carbonate (EC) by the conversion subsystem, and further subjecting the ethylene carbonate to a catalytic reaction with hydrogen to obtain methanol and a glycol; providing the supercritical carbon dioxide and nanocellulose to make the supercritical carbon dioxide nanocellulose slurry by the utilization subsystem, and after adjusting the concentration of the made supercritical carbon dioxide nanocellulose slurry, combining the adjusted supercritical carbon dioxide nanocellulose slurry with the material particles to extrude into a supercritical carbon dioxide nanocellulose foam material; preparing the supercritical carbon dioxide nanocellulose slurry by the supercritical refining and preparation of nanocellulose unit; preparing the supercritical carbon dioxide nanocellulose foam material by the supercritical carbon dioxide nanocellulose foaming material unit; wherein the energy subsystem is configured with a solar power generation and wind a power generation to provide clean power, and the power generated by residual heat recovery power and hydrogen gas power generation is also supplemented and deployed by the energy subsystem; wherein the energy subsystems not only has the power for each subsystem and unit of the flue gas recycling system stably distributed but also provides the required power for power distribution, lighting distribution, fire distribution, monitoring power distribution, and security distribution thereof.

A. The Combined Decontamination and Dust Removal Unit the combined decontamination and dust removal unit removes dust particles, nitrogen oxides, sulfur oxides and trace elements from the flue gas by a dry adsorption tower or an alkali absorption tank and a multi-stage dust collector, the trace elements include heavy metals such as mercury, selenium, and arsenic; wherein the dust particles are used in the supercritical carbon dioxide nanocellulose foaming material unit of the utilization subsystem as fillers in producing foams; wherein the nitrogen oxides and sulfur oxides are collected in the form of nitrate and sulfate by a sulfur oxynitride treating system for extracting and manufacturing fertilizer;

in the prior art, the combined removal process of dust and dust particles from flue gas includes: wet method, semi-dry method and dry method; wet method mainly uses oxidant oxidation technology, semi-dry method mainly includes spray dryer, electron beam method, pulse corona method and flue gas circulating fluidized bed technology; dry method mainly includes solid phase adsorption and gas phase oxidation technology; dry method has less investment in equipment than wet and semi-dry method, and does not generate secondary pollution such as waste liquid. More broad utilization prospects.

Commonly used adsorbents for dry processes include activated carbon, activated coke, zeolite molecular sieves, etc.; the key point of the dry method is how to process desulfurization, denitrification and demercuration process and the adsorbent regeneration processes at the same time, the dry method of the combined decontamination and dust removal unit is described as follows:

using active pyromagnetic supported silver-bearing zeolite and supported SCR catalyst as adsorbents, including magnetic $Fe_3O_4$ particles, silver nanoparticles, zeolite and activated coke, $V_2O_5$—$WO_3$/$TiO_2$ oxide; wherein the most commonly used SCR catalyst is $V_2O_5$—$WO_3(MoO_3)$/$TiO_2$ series ($TiO_2$ as the main carrier and $V_2O_5$ as the main active ingredient);

wherein the flue gas includes flue gas from a thermal power plant, a thermal power plant, a petroleum processing plant, a steel plant, a cement (phosphorus magnesium) plant, a chemical plant, etc., more particularly a flue gas from a coal-fired power plant, a water gas power plant, and a gas power plant;

wherein the flue gas from the flue gas source is fed into the dry adsorption tower 12, and adsorbed by the activated coke magnetic silver-loaded zeolite and supported by the SCR catalyst, and a combined process of sulfur removal, mercury removal and nitride removal from the flue gas is processed, and then, by passing through the multi-stage dust collector 13 to separate the duct particles from the flue gas to obtain the pure flue gas, and the pure flue gas is conveyed into a flue gas tank to store; wherein the solid phase mixture is collected from the dry adsorption tower and the lower part of the multi-stage dust collector, and the solid phase mixture is conveyed to a magnetic separator 14 to separate the metal from the solid phase mixture, and a magnetic catalyst is conveyed to the regenerator 15 for catalyst regeneration and recycling, the dust is recycled to produce byproduct, the mercury is recycled separately.

The wet process of the combined decontamination and dust removal unit is described as follows: the flue gas from the flue gas source is introduced, wherein the flue gas is treated sequentially by the following steps 1. by a SCR denitration device, using SCR catalyst: $V_2O_5$—$WO_3$ ($MoO_3$)/$TiO_2$ to selectively catalyze reduction to remove nitrogen oxides from flue gas;

2. by a waste water heat recovery device, recovering the residual heat to adjust the temperature of the flue gas to about 95° C., below the acid dew point, which is beneficial to the adsorption of trace elements and the removal of dust;

3. by a electrostatic precipitator and a bag filter, removing 90% of the solid particles of the soot;

4. by a wet-desulfurization device equipped, the water is conveyed by a transfer pump 7 in a desulfurization tower 1, with a spray layer of the spray coverage rate reached above 250%, absorbing and removing the sulfur oxides and the remaining nitride;

4.1 by a mechanical mist eliminator and a wet mist eliminator, eliminating mist and removing 10% of the dust again;

conveying the pure flue gas into the capture subsystem after desulfurization; conveying the desulfurized wastewater into the desulfurization wastewater treatment device;

5. in the desulfurization wastewater treatment device, the wastewater passing through a steam separator including chlorine ions and various heavy metal components is soften and concentrated by a softening concentrator, and the softened concentrated water is transferred and sprayed into the high temperature denitration flue gas to evaporate and remove crystallization dust again, so as to achieve zero discharge operation of wet desulfurization wastewater;

6. a mercury catalyst is fed into the flue gas in the electrostatic precipitator to oxidize element mercury to mercury ions by a feeder, and then removing the mercury ions and the sulfur dioxide by the sequence wet desulfurization device.

The sulfur dioxide removal rate reached 99.5%; the dust particle removal rate was 100%.

B. The Capture Subsystem the capture subsystem is used to treat the carbon dioxide and moisture from the flue gas after dust removal, desulfurization and denitration, wherein the flue gas is from the factory, the power plant and the refinery; wherein the flue gas stored in a flue gas tank respectively passes through the water recovery unit and the carbon dioxide capture unit recovering the water gas and carbon dioxide from the flue gas; the water is stored in a water tank, and carbon dioxide is stored in a carbon dioxide tank, and carbon dioxide stored in the carbon dioxide tank is converted into supercritical carbon dioxide through a supercritical pump and then stored in a supercritical carbon dioxide tank;

the carbon dioxide recovery unit of the capture subsystem comprises an absorption/desorption unit or an ammonia spray absorption tower 2 and a purification unit; carbon dioxide is absorbed by the carbon absorbent in a absorption tower of the absorption/desorption unit, equipped with a heat exchanger, an absorbent tank and a gas-liquid separator, and is desorbed by a regenerated carbon absorbent in a regeneration tower 3, the carbon absorbent is recycled; the desorbed carbon dioxide of the regeneration tower is sequentially subjected to residual sulfur removal, dewatering and other trace element removal through a double desulfurization bed 8, a drying bed 9, and an adsorption bed 10 of the purification unit and finally the carbon dioxide is purified to 99.9% purity; and the purified carbon dioxide is stored in the carbon dioxide tank;

the decarbonization aqueous solution for decarbonization uses MEA, DEA and AEEA mainly as the main absorbent, MDEA as the auxiliary absorption, composed of a plurality of active components with strong absorption ability, a preservative and a corrosion inhibitor, although each component has advantages, the disadvantage is that the average decarburization is generally low, the regeneration energy consumption is high, the solvent circulation rate is high; and the equipment is severely corroded; (ethanolamine, diethanolamine, hydroxyethylethylenediamine, methyldiethanolamine).

The invention adopts a composite decarbonization aqueous solution comprising a main absorption component, an auxiliary absorption component, an activation component, a corrosion inhibitor, an antioxidant and water; wherein the main absorption component comprise hydroxyethylethylenediamine AEEA, and the auxiliary absorption includes 2-amino-2-methyl-1-propanol AMP, MDEA and triethanolamine TEA, the active components comprise MEA, DEA and piperazine PZ, the corrosion inhibitor includes sodium citrate, and the antioxidants include sodium sulfite and copper acetate; the decarbonization aqueous solution has the advantages of large absorption capacity, high purification degree, high desorption rate and low regeneration energy consumption; and is suitable for using in the mixture gas with 3%-70% carbon dioxide from the flue gas.

The formula: mass fraction of hydroxyethylethylenediamine is 5%-35%; mass fraction of additive is 5%-30%; mass fraction of activated component is 1%-10%; mass fraction of corrosion inhibitor is 0.05%-1.0%; mass fraction of antioxidant content is 0.05%-1.0%; mass fraction of total butylamine is 35%-55%; mass fraction of water is 45%-65%.

The active component solute of the decarbonized aqueous solution is generally within 30%, and the remaining 70% solvent is water, and the solution that absorbs $CO_2$ (commonly known as the rich liquid) needs to be heated to a temperature of 100° C.-120° C. during the regeneration process, with the decomposition of the absorption intermediate at the temperature mentioned above, a large amount water will evaporate to result in excessive regeneration energy consumption; and the evaporated water needs to be condensed at the top of the regeneration tower to maintain the water balance in the system, the amount of condensed water required for the condensation process is large, so the cost of the decarbonized aqueous solution has been high, and the economic benefits cannot be optimized.

Preferably, the present invention also adopts a non-aqueous decarburization solution: N-ethylethanolamine is the solute; N,N-diethylethanolamine is the solvent; the weight percent of the solute in the non-aqueous decarburization solution is in the range of 20-80 wt %, and the rest is the solvent; the non-aqueous decarburization solution is used under the conditions of a pressure range of 0-1.2 MPa and in the temperature range of 10-140° C.; the solvent can also be used as a reactant in the process to increase the absorption, the desorption rate and desorption rate at the same time.

C. The Water Recovery Unit the water recovery unit uses a double-pipe water and heat recovery device to recover water and residual heat from the flue gas; the residual heat is used for heat pump power generation or steam turbine power generation, and the water is transferred and stored in the water tank for electrolytic hydrogen production or process water; wherein the double-pipe water and heat recovery device can respectively applied to the flue gas source, the combined decontamination and dust removal unit, the capture subsystem, the conversion subsystem, the utilization subsystem, and the energy source subsystem of the flue gas total recycling system, in the subsystem, dual-pipe water and heat recovery devices with various specifications are respectively produced according to the design principle of the double-pipe water and heat recovery device and the real function of the each subsystem and unit, respectively applied to each subsystem and unit of the flue gas total recycling system;

the double-pipe water and heat recovery device, as shown in the schematic diagram, relates to condensed water recovery, high-temperature heat or waste heat recovery, and waste water and waste residue treatment; the condensed water is transferred and stored in the water tank for use standby, high-temperature heat or residual heat is used for steam turbine power generation or heat pump power generation, it can also be used for the flue gas total recycling system heating or external heating.

The double-tube water and heat recovery device uses double heat pipe technology to recover heat or residual heat from the flue gas, it uses double refrigerant technology to recover gaseous water from the flue gas, efficiency of the integrated design of the water and residual heat recovery is high, and it is convenient for the subsequent process to comprehensively utilize water and residual heat.

D. Hydrogen Production Unit the hydrogen production unit adopts the electrolysis method to produce hydrogen and oxygen gas by using water captured by the water recovery unit; a water gas unit uses oxygen which is the production of the hydrogen production unit as comburent to burn the water gas to generate power, the power generated by the water gas unit is provided to the flue gas total recycling system; the high-purity hydrogen produced by the water gas unit and the hydrogen produced by the hydrogen-production unit are stored in the hydrogen tank together; for the non-water-gas power plant, the present invention uses integrated water gas system as a combined facilities of energy, hydrogen and oxygen of the total recycling system.

E. The Conversion Subsystem the conversion subsystem utilizes hydrogen produced by the hydrogen production unit or/and the water gas unit to carry out heterogeneous chemical reaction of the catalyst, hydrogen, carbon dioxide and a solid catalyst under the catalysis of a copper-based nano catalyst; a fixed-bed reactor is used as a catalytic reactor and a microplate reactor as a synthesis reactor placed bef. and aft., carbon dioxide is converted into methanol and a glycol by selective hydrogenation of cyclic carbonate intermediate;

1. conversion technology scheme: $CO_2$ is converted into methanol by catalytic hydrogenation, by using heterogeneous catalytic reaction system, wherein there are many kinds of copper-based catalyst carriers, and characteristics of the nano catalyst are high specific surface area, high dispersion, good thermal stability and high surface energy, and the surface active sites, the conversion rate of converting $CO_2$ into methanol and glycol by selective hydrogenation of cyclic carbonate intermediate and cyclic carbonate is up to 100%, the selectivity of methanol is up to 99%, the selectivity of glycol is in the range of 95-99%, the copper-based catalyst can be stably recycled after being filtered or centrifuged;

the processes of conversion of carbon dioxide to methanol and glycol at the same time by selective hydrogenation of cyclic carbonate intermediate are:

using a supported catalyst having a non-noble metal Cu as an active component with good hydrogenation activity, selectivity and stability to cyclic carbonate under mild conditions; wherein cyclic carbonate is a compound having at least three carbon atoms cyclic ring structure, having a chemical structural formula of:

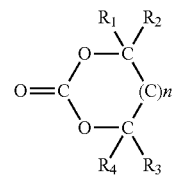

wherein each R1, R2, R3, R4, is independently selected from hydrogen, C1-12 alkyl, and optionally substituted aromatic ring, n is 0 or 1;

the concentration of the cyclic carbonate reaction solution is in the range of 10-100%, and the solvent of the cyclic carbonate reaction solution is selected from tetrahydrofuran or 1,4-dioxane;

$CO_2$+ethylene oxide–ethylene carbonate

Ethylene carbonate+H2–methanol+ethylene glycol+ethylene oxide

Wherein the reaction condition is mild, the process is the green reaction with high efficiency, the catalyst preparation process is simple, the production cost is low, the catalytic performance is stable, and the production processes of industrialization is easy;

wherein the addition reaction of ethylene oxide and carbon dioxide for preparing ethylene carbonate is an exothermic and volume-reducing reaction. From the aspect of chemical equilibrium, the conditions of low temperature and high pressure are favorable for the reaction, and the copper-based nano catalyst is selected to make the reaction proceed smoothly, the system is a heterogeneous catalytic system;

wherein ethylene carbonate (EC) is an excellent organic solvent that can dissolve a variety of polymers; it can be used as an organic intermediate to replace ethylene oxide in dioxylation reaction; and it is a main material for the production of dimethyl carbonate by transesterification; the transesterification method is a method for preparing ethylene carbonate by transesterification of diethyl carbonate and ethylene glycol, and the process is not complicated and the key point is to apply a suitable catalyst to increase the reaction temperature of the system, and speed up the reaction.

2. conversion reactor configuration: the double-loop circulating structure of the fixed-bed reactor and the microplate reactor is adopted, the catalytic reactor is the fixed bed reactor, the synthesis reactor is the microplate reactor, and the catalytic reactor and the synthesis reactor are double-loop circulating structure, a copper boron nano catalyst is used in the fixed bed reactor, a copper plate nano catalyst is used in the microplate reactor; wherein the hydrogen and carbon dioxide gas sent to the fixed bed reactor through a heat exchanger by a transfer pump react with the ethylene oxide in the liquid phase to form the ethylene carbonate intermediate, under the catalyzed reaction of the copper boron nano catalyst, the methanol and glycol are produced in hydrogen reduction reaction; wherein after transferring heat by passing through the heat exchanger and cooling down by a condenser 11, the reaction gas is sent to a gas-liquid separator 6 to separate into the gas and liquid, the gas is sent the microplate reactor, the liquid is transferred and stored in an alcohol tank; wherein in the microplate reactor, the gas and the ethylene carbonate in the liquid phase react with hydrogen under the catalyzed reaction of the copper ruthenium nano catalyst to produce methanol and glycol; after passing through the heat exchanger and the condenser 11, the reaction mixture is sent to a gas-liquid separator 6, and the liquid phase product is transferred and stored in a glycol tank, the gas phase product is returned back and cyclically reacted with hydrogen and carbon dioxide gas;

a stirring reaction accelerator 16 is respectively disposed at top of the catalytic reactor and the synthesis reactor.

3. Heterogeneous Catalytic System:

(1) Liquid phase: the solvent is tetrahydrofuran or 1,4-dioxane; the solute is ethylene oxide and ethylene carbonate;

(2) Solid phase: silica-supported copper-nano catalysts is used, copper boron nano catalysts is used in the fixed bed reactor; copper plated nano catalysts is used in the microplate reactor;

(3) Gas phase: Hydrogen, Carbon Dioxide Gas, Reaction Cycle Mixed Gas;

4. System Composition and Ratio:

The supported copper catalyst is used for hydrogenation of cyclic carbonate to make methanol and glycol, the composition of catalyst is Cu/X or Cu-M/X, wherein the carrier X is any one or two of the composites of $SiO_2$, $Al_2O_3$, MgO, $ZrO_2$, ZnO, the auxiliary agent M is any one or more metal selected from Ba, Mn, Y, La, Ce, Sm, Ga, B, and the Cu metal-loading in the catalyst is 5-70.%, preferably 10-60%, the loading of the auxiliary agent M in the catalyst is 0.0-15% oxide, preferably 0.1-12% oxide, and the balance is an oxide carrier; the reaction temperature is 120-180° C., the hydrogen pressure is 2-8 MPa, the reaction time is 4-20 h;

Cu metal-loading in the catalyst is preferably 10-60%, the loading of the auxiliary agent M in the catalyst is preferably 0.1-12% oxide, and the balance is an oxide carrier.

5. Reaction conditions: reaction temperature is 120-180° C., hydrogen pressure is 2-8 MPa, reaction time is 4-20 h.

6. Preparation of active copper-based nano catalyst: the catalyst precursor is prepared by a conventional co-precipitation method or a deposition precipitation method, and the catalyst precursor is dried at 80-120° C. for 10-13 hours, and calcined at 300-600° C. for 3-8 hours; Boron additives and ink are soluble salts, specifically selected from nitrate or acetate, non-metal B is selected from boric acid or boron oxide, co-precipitated with copper salt, copper nitrate or copper acetate, or based on Cu/X auxiliary catalyst precursor added by the upper volume impregnation method; activation of the catalyst precursor: at 250-500° C., reduction in hydrogen atmosphere for 2-6 h to obtain an active catalyst;

(1) Preparation of Copper Boron Catalyst: (43% Cu—$B_2O_3$/$SiO_2$)

Preparation of the precursor: Take 15.00 g of copper nitrate trihydrate and 25.00 g of 20% by mass of acidic silica sol into a round bottom flask, 125 mL of distilled water is added thereto to stir and disperse, precipitated with 10 wt % NaOH solution used as precipitant at pH≥10, then the temperature was raised to 80° C. for 4 h. After cooling and suction filtration, the pre-precursor is washed with distilled water until neutral PH and dried at 120° C. for 12 h, then crushed and sieved into nano-powder, thus the precursor is obtained;

Catalyst preparation: The precursor was impregnated with 3% $B_2O_3$ auxiliary agent by mass, described as follows: the 0.26 g of boric acid was weighed to add to a certain amount of distilled water to prepare a solution, and 4.90 g of the precursor was impregnated in an equal volume, and dried at 120° C. for 12 h, calcined at 500° C. for 3 hours in a muffle furnace, reduced and activated at 400° C. for 3 h in a hydrogen atmosphere, thus an active catalyst of 43% Cu—$B_2O_3$/$SiO_2$ was obtained (2) Preparation of Copper Ruthenium Catalyst: (43% Cu—$La_2O_3$/$SiO_2$)

Preparation of the precursor: Take 15.00 g of copper nitrate trihydrate, 25.00 g of of acidic silica sol with 25% by mass into a round bottom flask, add 125 mL of distilled water to stir, disperse and dissolve thereof, precipitate with 10 wt % NaOH solution which is used as precipitant until the pH≥10 and the temperature was raised to 80° C. for 4 h. After cooling and suction filtration, washing with distilled water to neutrality, drying at 120° C. for 12 h, grinding and sieving into nano-parts to obtain the precursor;

Catalyst preparation: The precursor was impregnated with $La_2O_3$ auxiliary agent with a mass fraction of 3%, as follows: 0.42 g of lanthanum nitrate hexahydrate was weighed, a certain amount of distilled water was added to prepare a solution, and an equal volume of 4.90 g of the precursor was impregnated at 120° C. After drying for 12 h, calcination at 500° C. for 3 h in a muffle furnace, and reduction and activation at 400° C. for 3 h in a hydrogen atmosphere, the active catalyst 43% Cu—$La_2O_3$/$SiO_2$ was obtained.

F. The Utilization Subsystem

The utilization subsystem comprises the supercritical refining and the preparation of nanocellulose unit, a supercritical carbon dioxide nanocellulose foaming material unit;

(1) the supercritical refining and preparation of nanocellulose unit comprises cellulose and a refining device;

wherein the particle size of the cellulose is in micrometer level, and the cellulose comprises any one or more of wood fiber, carbon or carbon fiber, silicon or silicon fiber, metal or metal fiber, and graphite or graphite fiber;

wherein the refining device is a fully sealed, high pressure resistant, waterless device, the cellulose is mixed with a supercritical carbon dioxide liquid by the refining device, and a refiner is used to grind micron-sized cellulose into nano-sized fibers, the nano-scale cellulose and supercritical carbon dioxide constitute a supercritical carbon dioxide nanocellulose slurry, referred to as a nano-slurry; wherein the amount of the nano-slurry content of the nano-slurry is greater than 1%;

wherein the refining device comprises a slurry tank 100, a refiner 200 and a conveyor 300; wherein the slurry tank 100, the refiner 200 and the conveyor 300 are connected in a sealed manner through a three-way valve 109, a vacuum valve 110 and a high pressure pipeline 12, and operated under supercritical conditions, the internal circulation flow is filled with a slurry 107 composed of liquid-phase supercritical carbon dioxide where the cellulose powder dissolved; the conveyor 300 is equipped with a pump motor 301 and a fluid pump 302 in a chassis 306, wherein the pump motor 301 drives the fluid pump 302 through a drive belt 305, sucks the slurry 107 from the slurry tank 100 to the pump inlet 303, and delivers the slurry 107 from the pump outlet 304 to a refiner 200 feed port 204 through the high pressure pipeline 112, the slurry 107 is conveyed to a place between a fixed grinding disc 207 and a rotating grinding disc 208 through a side flow passage 210, after finely ground and the slurry is introduced into a material cylinder 203 by a hollow rotating shaft 209, and is sent to the slurry tank 100 through a outlet 211 and the high pressure pipeline 112, thus the slurry 107 is formed into a circulating transport flow in a supercritical state.

A chassis 213 is arranged on the lower shaft of the refiner 200, and the hollow rotating shaft 209 driven by a grinding motor 202 through a drive belt 212 is displaced inside the chassis 213, and the hollow rotating shaft 209 drives the rotating grinding disc 208 to rotate at a high speed, and the superfine nano-grinding gears meshed with each other are arranged on the rotating grinding disc 208 and the fixed grinding disc 207 the fixed grinding disc, the micron scale cellulose is grinded into nanoscale cellulose by the superfine nano-grinding gears.

The slurry tank 100 is equipped with a temperature sensor 104, a pressure sensor, a density sensor and a particle size detecting sensor for detecting the temperature, pressure, density and cellulose particle size of the slurry 107 in the slurry tank 100, respectively, and the detected parameter information is displayed by the PLC controller.

A heater 103 and a cooler are disposed outside the slurry tank 100 for controlling the temperature of the slurry 107 in the supercritical state in the slurry tank 100.

A $CO_2$ liquid inlet 106 on the slurry tank 100 is used to feed the supercritical carbon dioxide liquid, and the pressure of the supercritical carbon dioxide is controlled by releasing or adding a carbon dioxide liquid controlled by the valve group and the vacuum valve 110 disposed on the $CO_2$ liquid inlet 106.

The slurry tank 100 further includes a mixer 101, a stirrer 102, a cleaning tank 108, a outlet 111, a cleaning agent 113 and a sewage outlet 114; the mixer 101 and the stirrer 102 are used for mixing and stirring the slurry 107 in the slurry tank 100, and the cleaning tank 108 is filled with the cleaning agent 113 for cleaning the refining device, and the sewage outlet 114 is for discharging the cleaning waste liquid.

The refiner 200 further includes a grinding body 201, a pressure gauge 205, a flow meter 206, the grinding body 201 is a housing of the refiner 200, and the pressure gauge 205 and the flow meter 206 are assembled on the high pressure pipeline 112 of the outlet for displaying the pressure and flow rate of the supercritical slurry.

(2) The supercritical carbon dioxide nanocellulose foaming material unit comprises an auxiliary device, a compounding device, an injection device, a twin-screw extruder, a foaming device, and a foaming material;

wherein the compounding device adjusts the ratio of supercritical carbon dioxide and nanocellulose in the nano slurry, and releases carbon dioxide therein to increase the content of nanocellulose in the nano slurry, after releasing the carbon dioxide through the compounding device. The ratio of carbon dioxide to nanocellulose in the nanoslurry is (30%-70%): (70%-30%) (wt %) to keep certain amount of nanocellulose in the foaming material, and improve the performance thereof; the compounding device is connected with a nano-slurry storage tank, and the nano-slurry storage tank is used for storing and supplying the maked nano-slurry;

wherein the amount of carbon dioxide dissolved in the foaming material is positively correlated with the pressure of supercritical carbon dioxide; when the pressure is 5 MPa, the amount of dissolved carbon dioxide is 3%; when the pressure is 15 MPa, the amount of dissolved carbon dioxide is 10%. The pressure of present invention is about 20 MPa in order to increase the amount of dissolved carbon dioxide to a higher percentage;

wherein the utilization system mixes the adjusted nano-slurry, supercritical carbon dioxide, and accelerator to a design formula, and uniformly mixes to obtain the supercritical liquid material by a high-pressure mixer; further, the supercritical liquid material is injected into the twin-screw extruder at a high pressure through the nanometer cellulose injection device; and the particles material are fed into the twin-screw extruder at the same time, then the supercritical liquid material is melt-mixed with thereof, and extruded through a mold to obtain an extruded product. The extruded product is foamed by a foaming process to obtain a foam material product;

wherein the auxiliary device is equipped with a supercritical carbon dioxide tank supplying a required supercritical carbon dioxide liquid, a CO2 pressure stabilizer, a high pressure pump, a CO2 thermostat and a mass flow meter for quantitative measurement of providing the requited supercritical carbon dioxide; the high pressure pump and a mass flow is used for quantitative measurement of providing accelerating agent;

wherein the material particles include plastic particles or powders, cement particles or powders, glass particles or powders; the foaming materials include foamed plastics, foamed cement, foamed glass, and the foamed materials include sheets, plate, profile, block or structure.

The performance index of the foaming material is: (taking PP foam material as an example).
1. the content of nanocellulose is: 1%-5%;
2. the modulus of elasticity is: 3 GPa-10 GPa;
3. the heat distortion temperature (HDT) is: 130° C.-150° C.;
4. the intensity is: 1000 KPa-3000 KPa.

In the prior art, the strength of the related domestic foam product only is 150 KPa-500 KPa; the strength of the related foam product in the United States only is 1000 KPa.

G. The Energy Subsystem

The energy subsystem is used to comprehensively regulate and configure the power consumption and heat distribution and recovery of each subsystem, and the purpose is to satisfy the electricity and heat consumptions of each subsystem by fully using electricity or heat from clean energy power generation, hydrogen power generation, waste heat recovery and power generation, and the self-sufficiency of the entire total recycling system is finally realized;

therefore, the energy subsystem is equipped with the solar power generation device and the wind power generation device, and storing energy by electrolyzing water to make hydrogen, and when the power generated by solar power generation and wind power generation is rich, the excess energy is stored in the form of electrolytic hydrogen; when the system needs additional power, the needed power can be provided by the gas generator through burning the hydrogencan gas.

The system makes full use of the residual heat of each subsystem by heat pump and waste heat recovery technology, and the excess heat is stored in the form of supercritical carbon dioxide, and the stored heat energy can be used by releasing heat through the supercritical carbon dioxide when needed.

The energy subsystem further comprises high-purity oxygen generated when water is electrolyzed, and the electrolytic oxygen is used for coal-fired power generation of a water gas power plant, and at the same time, high-purity hydrogen after combustion of the water gas power plant is obtained, by storing or using the obtained hydrogen in the conversion subsystem, the whole system is operated in a comprehensive cycle and comprehensive resource mode; through the capture, conversion and utilization of carbon dioxide, the final output is methanol, glycol, foams, which constitutes the material balance of the system; the integration of the energy system enables the utilization of clean energy, hydrogen energy and system heat energy to achieve self-sufficiency in energy consumption of the entire system, and also output part of heat energy, electric energy or hydrogen energy. Thereby full quantification of energy utilization and full quantification of flue gas utilization are achieved The energy subsystem uses solar energy and wind energy without carbon dioxide emissions, in the initial stage of the total resource system, it is still necessary to use market-oriented electric energy and heat energy as the initial system starting energy.

The beneficial effects of the present invention are: a combination technology of a total recycling of flue gas from factory, power plant and refinery and conversion into high added value is designed for the first time; carbon dioxide emitted by two major industries, thermal power plants in the energy industry and petroleum processing plants, is recycled and conversed into high value-added product such as methanol and glycol and a variety of ultra-light and ultra-strong nanocellulose foam material to achieve reduction of carbon dioxide emission, conversion and utilization of carbon dioxide; the carbon dioxide conversion rate is improved through conversion process of the copper-based nano catalyst, carbon dioxide and hydrogen; the dust particles and carbon dioxide are used to manufacture high value-added products, with solar energy and wind power generation system to cut off the source of smog and PM2.5 to be a closed carbon loop; the regenerative energy complements the fossil energy to thoroughly solve the problem of air pollution and global greenhouse effect.

The above description of the disclosed embodiments enables those skilled in the art to make or use the invention. Various modifications to these embodiments are obvious to those skilled in the art, and the general principles defined herein may be implemented in other embodiments without departing from the spirit or scope of the invention. Therefore, the present invention is not to be limited to the embodiments shown herein, but the scope of the invention is to be accorded.

The invention claimed is:

1. A total recycling system of capturing, conversion and utilization of flue gas from factory, power plant and refinery comprising an energy subsystem, a capture subsystem, and a conversion subsystem, an utilization subsystem, a water gas unit, a carbon dioxide capture unit, a hydrogen production unit, a water recovery unit, a combined decontamination and dust removal unit, a supercritical refining and preparation of nanocellulose unit, a supercritical carbon dioxide nanocellulose foaming material unit; wherein the flue gas includes dust particles, a gaseous compound, a trace element, carbon dioxide, and water vapor, wherein the gaseous compound includes at least nitrogen oxides and sulfur oxides; wherein the combined decontamination and dust removal unit is connected with the capture subsystem and the water gas unit; the conversion subsystem, the utilization subsystem, the water gas unit, the carbon dioxide capture unit, the hydrogen production unit, the water recovery unit, the supercritical refining and preparation of nanocellulose unit, and the supercritical carbon dioxide nanocellulose foaming material unit are connected with the capture subsystem;

wherein the flue gas total recycling system removes the dust particles and the gaseous compound by the combined decontamination and dust removal unit; capturing carbon dioxide by the carbon dioxide capture unit in the capture subsystem and pressurizing the captured carbon dioxide to supercritical carbon dioxide; recovering water vapor in the flue gas by the water recovery unit; decomposing the recovered water into hydrogen and oxygen through the hydrogen production unit, and feeding the oxygen into the water gas unit for combustion support to further obtain a high-purity hydrogen through the water gas unit; reacting the captured carbon dioxide having high stability and low energy with a high-energy ethylene oxide molecule to form ethylene carbonate(EC) by the conversion subsystem, and further subjecting the ethylene carbonate to a catalytic reaction with hydrogen to obtain methanol and a glycol; providing the supercritical carbon dioxide and nanocellulose to make supercritical carbon dioxide nanocellulose slurry by the utilization subsystem, and after adjusting the concentration of the made supercritical carbon dioxide nanocellulose slurry, combining the adjusted supercritical carbon dioxide nanocellulose slurry with material particles to extrude into a supercritical carbon dioxide nanocellulose foam material;

wherein the supercritical carbon dioxide nanocellulose slurry is prepared by the supercritical refining and preparation of nanocellulose unit; the supercritical carbon dioxide nanocellulose foam material is prepared by the supercritical carbon dioxide nanocellulose foaming material unit;

wherein the energy subsystem is configured with a solar power generation and wind a power generation to provide clean power, and the power generated by residual heat recovery power and hydrogen gas power generation is also supplemented and deployed by the energy subsystem; wherein the energy subsystems not only has the power for each subsystem and unit of the flue gas recycling system stably distributed but also provides the required power for power distribution, lighting distribution, fire distribution, monitoring power distribution, and security distribution thereof, through the capture, conversion and utilization of carbon dioxide, the final output is methanol, glycol, foams, which constitutes the material balance of the system; the integration of the energy system enables the utilization of clean energy, hydrogen energy and system heat energy to achieve self-sufficiency in energy consumption of the entire system, and also output part of heat energy, electric energy or hydrogen energy, so full quantification of energy utilization and full quantification of flue gas utilization are achieved;

the supercritical refining and preparation of nanocellulose unit comprises cellulose and a refining device;

wherein the particle size of the cellulose is in micrometer level, and the cellulose comprises any one or more of wood fiber, carbon or carbon fiber, silicon or silicon fiber, metal or metal fiber, and graphite or graphite fiber;

wherein the refining device is a fully sealed, high pressure resistant, waterless device, the cellulose is mixed with a supercritical carbon dioxide liquid by the refining device, and a refiner is used to grind micron-sized cellulose into nano-sized fibers, the nano-scale cellulose and supercritical carbon dioxide constitute a supercritical carbon dioxide nanocellulose slurry, referred to as-a nano-slurry; wherein the amount of the nano-slurry content of the nano-slurry is greater than 1%;

wherein the refining device comprises a slurry tank, a refiner and a conveyor; wherein the slurry tank, the refiner and the conveyor are connected in a sealed manner through a three-way valve, a vacuum valve and a high pressure pipeline, and operated under supercritical conditions, an internal circulation flow is filled with slurry composed of liquid-phase supercritical carbon dioxide where the cellulose is dissolved; the conveyor is equipped with a pump motor and a fluid pump in a chassis, wherein the pump motor drives the fluid pump through a drive belt, sucks the slurry from the slurry tank to the pump inlet, and delivers the slurry from the pump outlet to a refiner feed port through the high pressure pipeline, the slurry is conveyed to a place between a fixed grinding disc and a rotating grinding disc through a side flow passage, after finely ground and the slurry is introduced into a material cylinder by a hollow rotating shaft, and is sent to the slurry tank through an outlet and the high pressure pipeline, thus the slurry is formed into a circulating transport flow in a supercritical state;

a chassis is arranged on a lower shaft of the refiner, and the hollow rotating shaft driven by a grinding motor through a drive belt is displaced inside the chassis, and the hollow rotating shaft drives the rotating grinding disc to rotate at a high speed, and superfine nano-grinding gears meshed with each other are arranged on the rotating grinding disc and the fixed grinding disc the fixed grinding disc, the micron scale cellulose is grinded into nanoscale cellulose by the superfine nano-grinding gears;

the slurry tank is equipped with a temperature sensor, a pressure sensor, a density sensor and a particle size detecting sensor for detecting the temperature, pressure, density and cellulose particle size of the slurry in the slurry tank, respectively, and the detected parameter information is displayed by a PLC controller;

a heater and a cooler are disposed outside the slurry tank for controlling the temperature of the slurry in the supercritical state in the slurry tank;

a $CO_2$ liquid inlet on the slurry tank is used to feed the supercritical carbon dioxide liquid, and the pressure of the supercritical carbon dioxide is controlled by releasing or adding a carbon dioxide liquid controlled by a valve group and the vacuum valve disposed on the $CO_2$ liquid inlet;

the slurry tank further includes a mixer, a stirrer, a cleaning tank, the outlet, a cleaning agent and a sewage outlet; the mixer and the stirrer are used for mixing and stirring the slurry in the slurry tank, and the cleaning tank is filled with the cleaning agent for cleaning the refining device, and the sewage outlet is for discharging the cleaning waste liquid;

the refiner further includes a grinding body, a pressure gauge, a flow meter, the grinding body is a housing of the refiner, and the pressure gauge and the flow meter are assembled on the high pressure pipeline for displaying the pressure and flow rate of the supercritical slurry;

the supercritical carbon dioxide nanocellulose foaming material unit comprises an auxiliary device, a compounding device, an injection device, a twin-screw extruder, a foaming device, and a foaming material;

wherein the compounding device adjusts the ratio of supercritical carbon dioxide and nanocellulose in the nano-slurry, and releases carbon dioxide therein to increase the content of nanocellulose in the nano-slurry, after releasing the carbon dioxide through the compounding device; the ratio of carbon dioxide to nanocellulose in the nano-slurry is (30%-70%):(70%-30%) (wt %) to keep certain amount of nanocellulose in the foaming material, and improve the performance thereof, the compounding device is connected with a nano-slurry storage tank, and the nano-slurry storage tank is used for storing and supplying the made nano-slurry;

wherein the amount of carbon dioxide dissolved in the foaming material is positively correlated with the pressure of supercritical carbon dioxide; when the pressure is 5 MPa, the amount of dissolved carbon dioxide is 3%; when the pressure is 15 MPa, the amount of dissolved carbon dioxide is 10%; the pressure of present invention is about 20 MPa in order to increase the amount of dissolved carbon dioxide to a higher percentage;

wherein the utilization system mixes adjusted nano-slurry, supercritical carbon dioxide, and accelerator to a design formula, and uniformly mixes to obtain the supercritical liquid material by a high-pressure mixer; further, the supercritical liquid material is injected into the twin-screw extruder at a high pressure through the nanometer cellulose injection device; and the particles material are fed into the twin-screw extruder at the same time, then the supercritical liquid material is melt-mixed with thereof, and extruded through a mold to obtain an extruded product, the extruded product is foamed by a foaming process to obtain a foam material product;

wherein an auxiliary device is equipped with a supercritical carbon dioxide tank supplying a required supercritical carbon dioxide liquid, a $CO_2$ pressure stabilizer, a high pressure pump, a $CO_2$ thermostat and a mass flow meter for quantitative measurement of providing the requited supercritical carbon dioxide; the high pressure pump and a mass flow is used for quantitative measurement of providing accelerating agent;

wherein the material particles include plastic particles or powders, cement particles or powders, glass particles or powders; the foaming materials include foamed plastics, foamed cement, foamed glass, and the foamed materials include sheets, plate, profile, block or structure;

wherein the performance index of the foaming material is:
a. the content of nanocellulose is: 1%-5%;
b. the modulus of elasticity is: 3 GPa-10 GPa;
c. the heat distortion temperature (HDT) is: 130° C.-150° C.;
d. the intensity is: 1000 KPa-3000 KPa.

2. The total recycling system according to claim 1, wherein, the combined decontamination and dust removal unit removes dust particles, nitrogen oxides, sulfur oxides and trace elements from the flue gas by a dry adsorption tower or an alkali absorption tank and a multi-stage dust collector, the trace elements include heavy metals such as mercury, selenium, and arsenic; wherein the dust particles are used in the supercritical carbon dioxide nanocellulose foaming material unit of the utilization subsystem as fillers in producing foams; wherein the nitrogen oxides and sulfur oxides are collected in the form of nitrate and sulfate by a sulfur oxynitride treating system for extracting and manufacturing fertilizer;

the combined decontamination and dust removal unit for decontamination and removing dust together by wet method or dry method.

3. The total recycling system according to claim 1, wherein, the capture subsystem is used to treat the carbon dioxide and moisture from the flue gas after dust removal, desulfurization and denitration, wherein the flue gas is from the factory, the power plant and the refinery; wherein the flue gas stored in a flue gas tank respectively passes through the water recovery unit and the carbon dioxide capture unit recovering the water gas and carbon dioxide from the flue gas; the water is stored in a water tank, and carbon dioxide is stored in a carbon dioxide tank, and carbon dioxide stored in the carbon dioxide tank is converted into supercritical carbon dioxide through a supercritical pump and then stored in a supercritical carbon dioxide tank;

the carbon dioxide recovery unit of the capture subsystem comprises an absorption/desorption unit or an ammonia spray absorption tower and a purification unit; carbon dioxide is absorbed by the carbon absorbent in a absorption tower of the absorption/desorption unit, and is desorbed by a regenerated carbon absorbent in a regeneration tower, the carbon absorbent is recycled; the desorbed carbon dioxide of the regeneration tower is sequentially subjected to residual sulfur removal, dewatering and other trace element removal through a double desulfurization bed, a drying bed, and an adsorption bed of the purification unit and finally the carbon dioxide is purified to 99.9% purity; and the purified carbon dioxide is stored in the carbon dioxide tank;

a decarbonization aqueous solution or a non-aqueous decarbonization solution is used as carbon absorbent, wherein the decarbonization aqueous solution comprises ammonia water or a composite solution composed of a main absorption component, an assistance component, an activation component, a corrosion inhibitor, an antioxidant, and water, wherein the solute of the non-aqueous decarbonized solution is N-ethylethanolamine and the solvent is N, N-diethylethanolamine thereof.

4. The total recycling system according to claim 1, wherein, the water recovery unit uses a double-pipe water and heat recovery device to recover water and residual heat from the flue gas; the residual heat is used for heat pump power generation or steam turbine power generation, and the water is transferred and stored in the water tank for electrolytic hydrogen production or process water; wherein the double-pipe water and heat recovery device can respectively applied to the flue gas source, the combined decontamination and dust removal unit, the capture subsystem, the conversion subsystem, the utilization subsystem, and the energy source subsystem of the flue gas total recycling system, in the subsystem, dual-pipe water and heat recovery devices with various specifications are respectively produced according to the design principle of the double-pipe water and heat recovery device and the real function of the each subsystem and unit, respectively applied to each subsystem and unit of the flue gas total recycling system;

the double-pipe water and heat recovery device, in the schematic diagram, relates to condensed water recovery, high-temperature heat or waste heat recovery, and waste water and waste residue treatment; the condensed water is transferred and stored in the water tank for use standby, high-temperature heat or residual heat is used for steam turbine power generation or heat pump power generation, it can also be used for the flue gas total recycling system heating or external heating;

the double-tube water and heat recovery device uses double heat pipe technology to recover heat or residual heat from the flue gas, it uses double refrigerant technology to recover gaseous water from the flue gas, efficiency of the integrated design of the water and residual heat recovery is high, and it is convenient for the subsequent process to comprehensively utilize water and residual heat.

5. The total recycling system according to claim 1, wherein, the hydrogen production unit adopts the electrolysis method to produce hydrogen and oxygen gas by using water captured by the water recovery unit; a water gas unit uses oxygen which is the production of the hydrogen production unit as comburent to burn the water gas to generate power, the power generated by the water gas unit is provided to the flue gas total recycling system; the high-purity hydrogen produced by the water gas unit and the hydrogen produced by the hydrogen-production unit are stored in the hydrogen tank together; for the non-water-gas power plant, the present invention uses integrated water gas system as a combined facilities of energy, hydrogen and oxygen of the total recycling system.

6. The total recycling system according to claim 1, wherein, the conversion subsystem utilizes hydrogen produced by the hydrogen production unit or/and the water gas unit to carry out heterogeneous chemical reaction of the catalyst, hydrogen, carbon dioxide and a solid catalyst under the catalysis of a copper-based nano catalyst; a fixed-bed reactor is used as a catalytic reactor and a microplate reactor as a synthesis reactor placed, carbon dioxide is converted into methanol and a glycol by selective hydrogenation of cyclic carbonate intermediate, the conversion subsystem comprising conversion technology scheme, conversion reactor configuration, Heterogeneous catalytic system, System composition and ratio, Reaction conditions and Preparation of active copper-based nano catalyst.

7. The total recycling system according to claim 1, wherein the energy subsystem is used to comprehensively regulate and configure the power consumption and heat distribution and recovery of each subsystem, and the purpose is to satisfy the electricity and heat consumptions of each subsystem by fully using electricity or heat from clean energy power generation, hydrogen power generation, waste heat recovery and power generation, and the self-sufficiency of the entire total recycling system is finally realized;

the energy subsystem is equipped with the solar power generation device and the wind power generation device, and storing energy by electrolyzing water to make hydrogen, and when the power generated by solar power generation and wind power generation is rich, the excess energy is stored in the form of electrolytic hydrogen; when the system needs additional power, the needed power can be provided by the gas generator through burning the hydrogencan gas;

the system makes full use of the residual heat of each subsystem by heat pump and waste heat recovery technology, and the excess heat is stored in the form of supercritical carbon dioxide, and the stored heat energy can be used by releasing heat through the supercritical carbon dioxide when needed;

the energy subsystem further comprises high-purity oxygen generated when water is electrolyzed, and the electrolytic oxygen is used for coal-fired power generation of a water gas power plant, and at the same time, high-purity hydrogen after combustion of the water gas power plant is obtained, by storing or using the obtained hydrogen in the conversion subsystem, the whole system is operated in a comprehensive cycle and comprehensive resource mode.

\* \* \* \* \*